United States Patent
Akaba et al.

(10) Patent No.: US 9,891,338 B2
(45) Date of Patent: Feb. 13, 2018

(54) ELECTRIC NEAR-FIELD PROBE, CONTROL SYSTEM FOR SAME, AND PIEZOELECTRIC CRYSTAL DETECTOR

(71) Applicant: OSAKA UNIVERSITY, Suita-shi, Osaka (JP)

(72) Inventors: Hideo Akaba, Suita (JP); Hideo Itozaki, Suita (JP); Junichiro Shinohara, Chiba (JP); Yuji Miyato, Suita (JP); Fumiya Katsutani, Suita (JP)

(73) Assignee: OSAKA UNIVERSITY, Suita-shi (JP)

( * ) Notice: Subject to any disclaimer, the term of this patent is extended or adjusted under 35 U.S.C. 154(b) by 126 days.

(21) Appl. No.: 14/782,728

(22) PCT Filed: Apr. 3, 2014

(86) PCT No.: PCT/JP2014/059820
§ 371 (c)(1),
(2) Date: Oct. 6, 2015

(87) PCT Pub. No.: WO2014/171342
PCT Pub. Date: Oct. 23, 2014

(65) Prior Publication Data
US 2016/0047932 A1  Feb. 18, 2016

(30) Foreign Application Priority Data

Apr. 17, 2013  (JP) .................................. 2013-086553

(51) Int. Cl.
*G01R 29/08* (2006.01)
*G01R 29/22* (2006.01)
(Continued)

(52) U.S. Cl.
CPC .......... *G01V 3/02* (2013.01); *G01N 29/2443* (2013.01); *G01R 29/0814* (2013.01);
(Continued)

(58) Field of Classification Search
CPC combination set(s) only.
See application file for complete search history.

(56) References Cited

U.S. PATENT DOCUMENTS 3,417,329 A * 12/1968 Landis ................ G01N 27/025
324/445
7,132,942 B1  11/2006 Buess et al.

FOREIGN PATENT DOCUMENTS

| JP | 62-230115 A | 10/1987 |
| JP | 2001-159648 A | 6/2001 |
| JP | 2011-69630 A | 4/2011 |

OTHER PUBLICATIONS

International Search Report, issued in PCT/JP2014/059820, dated Jul. 15, 2014.
(Continued)

*Primary Examiner* — Minh Phan
(74) *Attorney, Agent, or Firm* — Birch, Stewart, Kolasch & Birch, LLP

(57) ABSTRACT

Provided is a compact and lightweight electric field probe which has a transmitting/receiving function whereby piezoelectric crystals can be excited through the application of an alternating current electric field thereto, and piezoelectric effect signals can be detected with sufficient sensitivity. Also provided are a control system for the same, and a piezoelectric crystal detector. The electric near-field probe is provided with a capacitor, in which the space between two metal plates that are positioned parallel to each other is filled by a conductor or air, and a series resonance circuit, which has a prescribed resonance frequency and is connected in series to an inverter that is formed by winding a conductive wire around a toroidal core. The electric near-field probe is configured such that: an electric near-field, which originates from the leakage electric field from the capacitor generated by the application of alternating current voltage to the series (Continued)

resonance circuit, is transmitted to the piezoelectric crystals, and the piezoelectric crystals are excited; and the piezoelectric effect signal, which is generated by the excited piezoelectric crystals, is received by the capacitor, and is detected by the series resonance circuit. The control system is for said electric near-field probe.

20 Claims, 17 Drawing Sheets

(51) Int. Cl.
    *G01V 3/02*         (2006.01)
    *G01N 29/24*       (2006.01)
    *G01V 3/08*         (2006.01)

(52) U.S. Cl.
    CPC ......... *G01R 29/0878* (2013.01); *G01R 29/22* (2013.01); *G01V 3/088* (2013.01)

(56) References Cited

OTHER PUBLICATIONS

Rayner et al., "Narcotics detection using piezo-electric ringing", The International Society for Optics and Photonics Proc., 1997, vol. 2936, pp. 31-38.

Written Opinion of the International Searching Authority, issued in PCT/JP2014/059820, dated Jul. 15, 2014.

* cited by examiner (a)
Parallel Plate Capacitor (Cross Section)

Parallel Plate Capacitor (Top)

to Transmission and Reception Circuit (b)

ELECTRIC NEAR-FIELD PROBE, CONTROL SYSTEM FOR SAME, AND PIEZOELECTRIC CRYSTAL DETECTOR

FIELD OF THE INVENTION

The present invention relates to: an electric near-field probe having a function of transmission and reception capable of exciting a crystal having a piezoelectric effect, that is, a piezoelectric crystal, by an external electric field and of detecting a piezoelectric effect signal generated from the excited piezoelectric crystal; a control system for the same; and a piezoelectric crystal detector employing the electric near-field probe and the control system for the same.

BACKGROUND OF THE INVENTION

It is known that when an alternating electric field is applied, a piezoelectric crystal mechanically vibrates at a particular frequency. Then, even after application of the alternating electric field is stopped, the mechanical vibration is maintained with attenuation by a piezoelectric effect and thereby generates a new alternating electric field.

Thus, by detecting the newly generated alternating electric field as a piezoelectric effect signal with an electric field probe (an electric field type antenna), the presence or absence of a piezoelectric crystal can be detected in a non-contact (e.g., Non-patent Document 1).

At that time, in a case that an electric field probe having a function of both transmission and reception capable of also applying an alternating electric field to the piezoelectric crystal is employed as the electric field probe, detection of a piezoelectric crystal can efficiently be achieved.

Such piezoelectric crystals include illicit drugs such as cocaine and stimulant. Then, as a specific example that an electric field probe having a function of both transmission and reception is applied to detection of an illicit drug, a technique is proposed that: a capacitor constructed from two metal plates is employed and then an object to be inspected such as a bag is inserted between the metal plates; and then an alternating electric field is applied between the metal plates and thereby a piezoelectric effect signal from an illicit drug such as cocaine and stimulant is received so that a concealed illicit drug is detected in a sealed state in a non-contact (e.g., Patent Document 1).

PRIOR ART REFERENCE

Patent Document

Patent Document 1: U.S. Pat. No. 7,132,942

Non-Patent Document

Non-patent Document 1: T. Rayner et al., Narcotics detection using piezoelectric ringing, the international society for optics and photonics Proc., 1997, vol. 2936, pp. 31-38

SUMMARY OF THE INVENTION

Problems to be Solved by the Invention

Nevertheless, in the case of conventional art, as described above, it has not been expected that measurement is performed in a state that the entirety of an object to be inspected is inserted between the metal plates of a capacitor. Thus, size increase of the electric field probe and hence size increase of the detector have been unavoidable. Further, a to-be-inspected object having a size not insertable between the metal plates of the capacitor cannot be inspected.

Further, natural cocaine or the like contains an impurity also. This has caused another problem that sufficient detection sensitivity cannot be obtained in the conventional art. Thus, this technique has not been used in practice.

Thus, an object of the present invention is to provide: an electric field probe having a small size and a light weight and yet having a transmission and reception function of capable of applying an alternating electric field to a piezoelectric crystal so as to excite the piezoelectric crystal and also detecting a piezoelectric effect signal with a sufficient sensitivity; a control system for this; and a piezoelectric crystal detector.

Means for Solving the Problem

For resolving the above-mentioned problems, the present inventor has conceived that in contrast to the conventional art wherein measurement is performed in a state that an object to be inspected is inserted between the metal plates of a capacitor, when a capacitor in which the distance between the metal plates is reduced to reduce size and weight is employed for fabricating an electric near-field probe having a function of transmission and reception, size and weight reduction of the electric field probe can be achieved.

Specifically, attention has been focused on a fact that when a voltage is applied to a capacitor, a leakage electric field occurs in the outside of the metal plates. Then, it has been conceived that when an electric near-field caused by the leakage electric field is transmitted so that the piezoelectric crystal is vibrated at a particular resonance frequency and then an alternating electric field, that is, a piezoelectric effect signal, generated by the vibration is detected, the piezoelectric effect signal can be detected with a sufficient sensitivity without the necessity of inserting the to-be-inspected object between the metal plates. Hence size and weight reduction of the electric field probe can be achieved.

However, when the leakage electric field is to be used, simultaneously to occurrence of the electric near-field, an alternating magnetic near-field is generated in some cases. The generated alternating magnetic near-field causes vibration in the metal plates or the like, and thereby induces an alternating magnetic field signal (magnetic ringing) so as to disturb the receiving of the piezoelectric effect signal. This causes a possibility of degradation in the detection sensitivity.

Thus, the present inventor has investigated means of suppressing occurrence of the alternating magnetic field signal in the above-mentioned electric near-field probe. As a result, with focusing attention on the inductor of an LCR resonance circuit provided in the electric near-field probe, it has been conceived that an inductor constructed such that a lead wire is wound around a toroidal core is to be employed.

The LCR resonance circuit is constructed such that a capacitor (C) constructed by inserting air or a dielectric material between two parallel metal plates serving as conductors is connected to an inductor (L) in series. Here, R indicates a resistance component contained in the inductor, the capacitor, a wiring, a transmission amplifier, and the like.

Then, in the LCR resonance circuit, when an inductor constructed such that a lead wire is wound around a toroidal core is employed, the magnetic field generated from the inductor is confined so that leakage of the magnetic field can sufficiently be suppressed. As a result, occurrence of an alternating magnetic field signal (magnetic ringing) can be suppressed.

An electric near-field probe having the above-mentioned LCR resonance circuit can have a remarkably small size and a remarkably light weight in comparison with an electric field probe of the conventional art. Further, as described above, a piezoelectric crystal can be excited by an electric near-field generated by a leakage electric field and, at the same time, a piezoelectric effect signal can be detected in a state that leakage of a magnetic field is sufficiently suppressed. Thus, when the electric near-field probe is held by the hand like a handy type metal detector and then merely brought close to an object to be inspected such as clothes and a bag, the presence or absence of a piezoelectric crystal can be detected.

That is, the invention according to claim 1 is an electric near-field probe comprising a series resonance circuit that is constructed such that a
  capacitor constructed such that a space between two metal plates arranged in parallel to each other is filled with a dielectric material or air and
an inductor constructed such that a lead wire is wound around a toroidal core,
are connected in series and that has a predetermined resonance frequency,
wherein an electric near-field originating from a leakage electric field from the capacitor generated when an alternating voltage is applied to the series resonance circuit is transmitted to a piezoelectric crystal so that the piezoelectric crystal is excited and, at the same time,
a piezoelectric effect signal generated from the excited piezoelectric crystal is received by the capacitor so that the piezoelectric effect signal is detected by the series resonance circuit.

Next, in order to improve the detection sensitivity further, the present inventor has investigated a capacitor structure more advantageous in transmission of the leakage electric field and detection of the piezoelectric effect signal. As a result, it has been confirmed that when an opening part is provided near the center of the metal plate opposing the piezoelectric crystal, the electric field intensity immediately above the probe center can be increased and the detection sensitivity can be improved further.

That is, the invention according to claim 2 is the electric near-field probe according to claim 1, wherein an opening part is provided in a center portion of the metal plate opposing the piezoelectric crystal among the two metal plates constituting the capacitor.

Next, the present inventor has investigated a series resonance circuit (including a series resonance circuit whose equivalent circuit becomes the same) that permits efficient detection in the electric near-field probe. As a result, it has been confirmed that when a plurality of series resonance circuits having different resonance frequencies are provided, piezoelectric crystals having different resonance frequencies depending on the kind, the particle size, or the like can efficiently be detected by using one electric near-field probe.

That is, the invention according to claim 3 is the electric near-field probe according to claim 1 or 2, wherein the series resonance circuit is constructed from a plurality of series resonance circuits having different resonance frequencies.

Then, in such an electric near-field probe including a plurality of series resonance circuits, when an alternating voltage of a frequency corresponding to each resonance frequency is inputted, resonance can easily be achieved at each of the different resonance frequencies.

That is, the invention according to claim 4 is the electric near-field probe according to claim 3, wherein in each of the plurality of series resonance circuits, when an alternating voltage of a resonance frequency corresponding to each series resonance circuit is inputted, resonance is achieved.

Further, also when a modulated alternating voltage is inputted to an electric near-field probe having a series resonance circuit constructed from a plurality of series resonance circuits, resonance can easily be achieved at different resonance frequencies.

That is, the invention according to claim 5 is the electric near-field probe according to claim 3, wherein in the plurality of series resonance circuits, when a modulated alternating voltage is inputted, resonance is achieved.

The electric near-field probe according to the present invention is basically used in the outside of an electromagnetic shield. Then, when the electric near-field probe is used in the outside of an electromagnetic shield as such, the electric near-field probe becomes subject to control under Article 100 of Radio Act. Thus, the electric field intensity at a 30-m away position need be limited to 100 μV/m or lower.

Thus, in the electric near-field probe according to the present invention, it is preferred that the electric field intensity at a distance is suppressed to the regulation value or lower and yet the electric field intensity in the vicinity of the probe is increased as high as possible.

As a result of investigation, the present inventor has confirmed that when an electric near-field probe of gradio structure type constructed such that two capacitors having the same shape and the same size are horizontally arranged and aligned with a wiring connected in opposite polarity to each other is employed, a sufficient electric field intensity can be ensured and yet the electric fields at a distance can cancel out.

That is, the invention according to claim 6 is the electric near-field probe according to claim 1, wherein two capacitors having the same shape and the size are arranged and aligned in parallel to each other, then an inductor having the same shape and the size is connected to each capacitor, and then the capacitors are connected to each other in opposite polarity so as to be constructed in a gradio structure type.

In some cases, the electric near-field probe is used in an electromagnetic shielding environment. In such cases, a noise from the outside is reduced by the electromagnetic shielding environment. On the other hand, a noise from the reception circuit is not reduced. Thus, there is a possibility that the noise from the reception circuit becomes dominant and degrades the receiving sensitivity.

Thus, the present inventor has confirmed that when the series resonance circuit is constructed such that the amplification factor for the noise in the reception circuit at the time of receiving is reduced and yet the amplification factor for the piezoelectric effect signal received by the electric near-field probe is maintained large, degradation in the receiving sensitivity is not caused.

That is, the invention according to claim 7 is the electric near-field probe according to claim 1, wherein the series resonance circuit is provided with an amplification factor changing circuit constructed such that an amplification factor for a noise in a reception circuit can be reduced and yet an amplification factor for the piezoelectric effect signal received by the electric near-field probe can be maintained large.

Further, the present inventor has confirmed that when a series resonance circuit is provided such as to reduce a transient phenomenon occurring in the electric near-field probe after termination of a transmission signal, the receiving sensitivity can be improved.

That is, the invention according to claim 8 is the electric near-field probe according to claim 1, wherein the series resonance circuit is provided with an amplifier circuit for transmission constructed such as to reduce a fall time of a transient phenomenon occurring in the electric near-field probe after termination of a transmission signal.

Here, the amplification factor changing circuit and the amplifier circuit for transmission described above may be applied to a probe, especially, an electric near-field probe, constructed from another resonance circuit and then a similar effect can be obtained.

The above-mentioned electric near-field probe is controlled by an electric near-field probe control system described below.

That is, the invention according to claim 9 is an electric near-field probe control system for controlling the electric near-field probe according to any one of claims 1 to 8, wherein an alternating voltage is applied to the series resonance circuit having a predetermined resonance frequency so that an electric near-field originating from a leakage electric field generated by the capacitor is transmitted from the electric near-field probe so as to excite the piezoelectric crystal and, on the other hand, a piezoelectric effect signal generated from the excited piezoelectric crystal is received by the capacitor so that presence or absence or a property of the piezoelectric crystal is detected by the series resonance circuit.

The above-mentioned electric near-field probe control system can be contained in the form of a small and lightweight system. Then, a piezoelectric crystal can sufficiently be excited by an electric near-field originating from a leakage electric field and hence a piezoelectric effect signal can be obtained with sufficient detection sensitivity.

Further, the invention according to claim 10 is a piezoelectric crystal detector comprising the electric near-field probe according to any one of claims 1 to 8 and the electric near-field probe control system according to claim 9 and thereby detects presence or absence or a property of a piezoelectric crystal.

This is a piezoelectric crystal detector having: an electric near-field probe constructed in a small size and a light weight; and an electric near-field probe control system. Thus, a portable piezoelectric crystal detector can be provided that can easily be carried and can perform high-accuracy measurement in a short time.

Further, the invention according to claim 11 is the piezoelectric crystal detector according to claim 10, serving as an illicit drug detector.

As described above, in the electric near-field probe according to the present invention, when the probe is held by the hand and then held over an object like a handy type metal detector, a piezoelectric effect signal can be obtained with sufficient detection sensitivity. Thus, illicit drugs such as cocaine and stimulant composed of piezoelectric crystals can efficiently be detected.

Further, the invention according to claim 12 is the piezoelectric crystal detector according to claim 10, employed in a non-contact key system.

By constructing a non-contact key system in which unlock is performed when a piezoelectric crystal key in which a piezoelectric crystal is buried is hang over a piezoelectric crystal detector, high security performance can be provided.

Further, the invention according to claim 13 is a piezoelectric crystal detector, wherein a plurality of the electric near-field probes according to any one of claims 1 to 8 are arranged between the plate electrodes arranged in parallel to each other.

Further, the present inventor has investigated a piezoelectric crystal detector in which even for piezoelectric crystals distributed broadly, a piezoelectric effect signal can be received with a high sensitivity so that the piezoelectric crystals can efficiently be detected and searched out.

As such a piezoelectric crystal detector for detecting piezoelectric crystals distributed broadly, in the conventional art, there has been a piezoelectric crystal detector for performing transmission and reception by using plate electrodes (parallel plate electrodes) arranged in parallel to each other. Nevertheless, it has been difficult so far to receive a piezoelectric effect signal with sufficiently high sensitivity.

The present inventor has found that when a plurality of the electric near-field probes according to the present invention are arranged between the parallel plate electrodes and then parallel plate electrodes are used for transmission and each of the plurality of electric near-field probes having been arranged is used for receiving, the piezoelectric crystals distributed broadly can efficiently be detected and searched out.

That is, when an electric field is transmitted from such parallel plate electrodes, the electric field can be generated broadly. Thus, even piezoelectric crystals distributed broadly can sufficiently be excited so that a piezoelectric effect signal can be generated. Then, it has been found that when the piezoelectric effect signal is received by a plurality of the electric near-field probes according to the present invention, the piezoelectric effect signal can be received with a high sensitivity and hence the piezoelectric crystals can efficiently be detected and searched out, in comparison with a case that receiving is performed by parallel plate electrodes.

Further, in a case that receiving is performed by parallel plate electrodes, even when a piezoelectric crystal is moved in a horizontal direction so that the distance from the parallel plate electrodes is changed, the receiving sensitivity does not substantially vary. However, in a case that receiving is performed by an electric near-field probe, it has been found that when a piezoelectric crystal is moved in a perpendicular direction so that the distance from the parallel plate electrodes is changed, the receiving sensitivity varies. Thus, the receiving sensitivity is improved at a position close to the electric near-field probe so that the piezoelectric crystal can more efficiently be detected and searched out.

Then, the piezoelectric crystal detector having the above-mentioned configuration can be constructed such that a reception circuit is connected to each of the plurality of electric near-field probes and then a transmission circuit is connected to the parallel plate electrodes. Since these reception circuits and transmission circuit are inexpensive, the piezoelectric crystal detector can be provided at a low cost.

Here, these reception circuits and transmission circuit may be provided individually or, alternatively, may be provided in an integrated manner. Further, the entirety may be constructed and integrated into one transmission and reception circuit. In a case that the individual circuits are provided individually, a piezoelectric crystal detector having higher detection sensitivity can be provided. On the other hand, in a case that the individual circuits are provided in an integrated manner, a more compact piezoelectric crystal detector can be provided.

Further, when the transmission and reception circuit is used as a circuit connected to the electric near-field probe, in cooperation with the electric field transmitted from the electric near-field probe, the electric field spreads at a higher intensity over a wider region. Thus, piezoelectric crystals in a wider range can sufficiently be excited and hence a piezoelectric effect signal can more efficiently be received with a high sensitivity.

Effect of the Invention

According to the present invention, it can provide: an electric field probe having a small size and a light weight and yet having a transmission and reception function of capable of applying an alternating electric field to a piezoelectric crystal so as to excite the piezoelectric crystal and also detecting a piezoelectric effect signal with a sufficient sensitivity; a control system for this; and a piezoelectric crystal detector.

MODE OF IMPLEMENTING THE INVENTION

Figure 1:
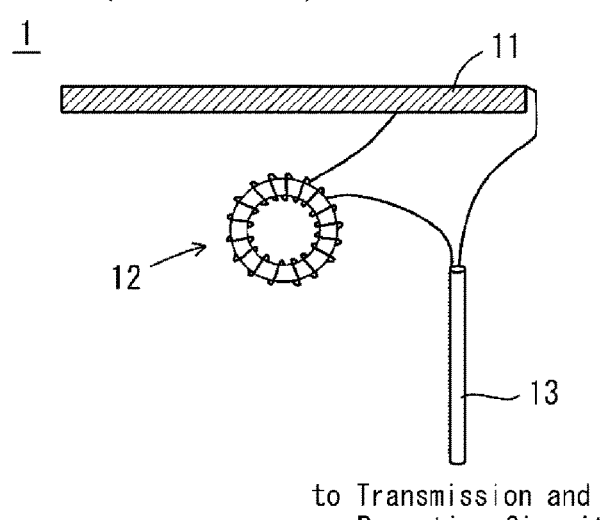
FIG. 1 is a diagram showing an example of configuration of a single frequency type electric near-field probe.
Figure 1:
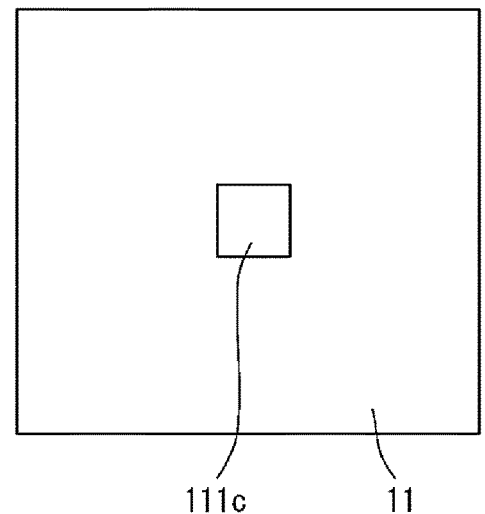
Figure 1:
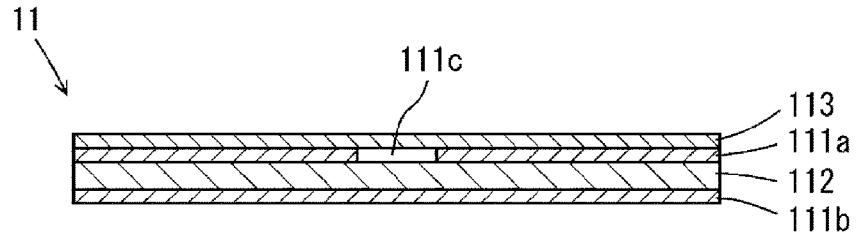

The present invention is described below in detail on the basis of an embodiment with reference to the drawings.
1. Electric Near-Field Probe
First, an electric near-field probe is described below.
(1) Single Frequency Type
FIG. 1 shows the configuration of a single frequency type electric near-field probe of the present invention. Part (a) is a schematic diagram (the right part is a top view and the left part is a sectional view). Part (b) is a sectional view schematically showing the configuration of a capacitor 11 shown in part (a).

As shown in FIG. 1(a), a single frequency type electric near-field probe 1 has an LCR resonance circuit using one capacitor 11 and one inductor 12. The capacitor 11 and the inductor 12 are connected in series and then connected to a transmission and reception circuit through a coaxial cable 13. One end of the inductor 12 is connected to the ground and hence maintained at a reference potential.

a. Capacitor

As the capacitor 11, a capacitor of parallel plate type preferable for formation of an electric field is employed. Specifically, the capacitor is constructed such that air or a dielectric material (polytetrafluoroethylene such as Teflon (registered trademark), a glass epoxy resin, or the like) is inserted between two metal plates fixed with a constant interval in between. By suitably changing the distance between the metal plates, the area, the kind of the dielectric material, the capacitance (C) of the capacitor can be adjusted.

Here, in the capacitor 11 shown in FIG. 1(b), numerals 111a and 111b indicate metal plates fabricated from a copper foil, numeral 112 indicates a dielectric material of polytetrafluoroethylene, and numeral 113 indicates a protection plate fabricated from plastics. When the protection plate 113 side is caused to oppose an object to be inspected, an electric near-field originating from a leakage electric field of the capacitor 11 is transmitted to a piezoelectric crystal serving as an object of measurement. Further, after the termination of transmission, a piezoelectric effect signal from the piezoelectric crystal is detected. The capacitor 11 having such a configuration can be fabricated, for example, by employing a microwave substrate fabricated by Polyflon Company (trade name: Cuflon) or the like.

In the above-mentioned capacitor 11, an opening part 111c is provided in the center portion of the metal plate 111a. As such, when the opening part 111c is provided in the center portion of the metal plate 111a opposing the piezoelectric crystal, the electric field intensity immediately above the probe center can be increased and, at the same time, the detection sensitivity can also be improved further. Here, the size and the shape of the metal plate 111a are not limited to particular ones. However, for example, in the case of a rectangular shape, a size of approximately 80×80 mm is preferable. Further, the size and the shape of the opening part 111c provided in the metal plate 111a like this are also not limited to particular ones. However, in the case of the metal plate 111a having the above-mentioned size, it is preferable that the opening part 111c is formed in a rectangular shape having a size of approximately 10×10 mm.

Here, a variable capacitor whose capacitance can be changed may be connected in parallel to the capacitor 11. In this case, the resonance frequency can suitably be adjusted in one electric near-field probe 1. This widens the range of application and hence is preferable.

b. Inductor

The inductor 12 is constructed such that a lead wire is wound around a toroidal core. When the fashion of winding of the lead wire is adjusted, the inductor 12 having a desired inductance (L) can be formed.

When the toroidal core is employed, a magnetic field generated from the inductor 12 can be confined so that leakage of the magnetic field can sufficiently be suppressed. Thus, occurrence of an alternating magnetic field signal (magnetic ringing) serving as an unnecessary signal at the time of measurement can be suppressed so that a piezoelectric effect signal can be detected with a high sensitivity.

c. Resonance Frequency

The electric near-field probe 1 having the above-mentioned configuration can perform both transmission of an alternating electric field and receiving of a piezoelectric effect signal. Then, on the basis of the inductance (L), the capacitance (C), and the resistor (R), a resonance frequency corresponding to an object piezoelectric crystal is set up. For example, in the case of inductance L=80.8 pH, capacitance C=167 pF, and R=6.8Ω, the resonance frequency is set to be 1.37 MHz. Here, the resonance frequency of the object piezoelectric crystal varies depending on the shape and the kind of the piezoelectric crystal. Even in piezoelectric crystals of the same kind, the resonance frequency varies depending on the size of the crystal grains or the like. Specifically, a large particle in the order of several centimeters has a resonance frequency in kHz band and a small particle in the order of several millimeters has a resonance frequency in MHz band.

(2) Plural Frequency Type

Figure 2:
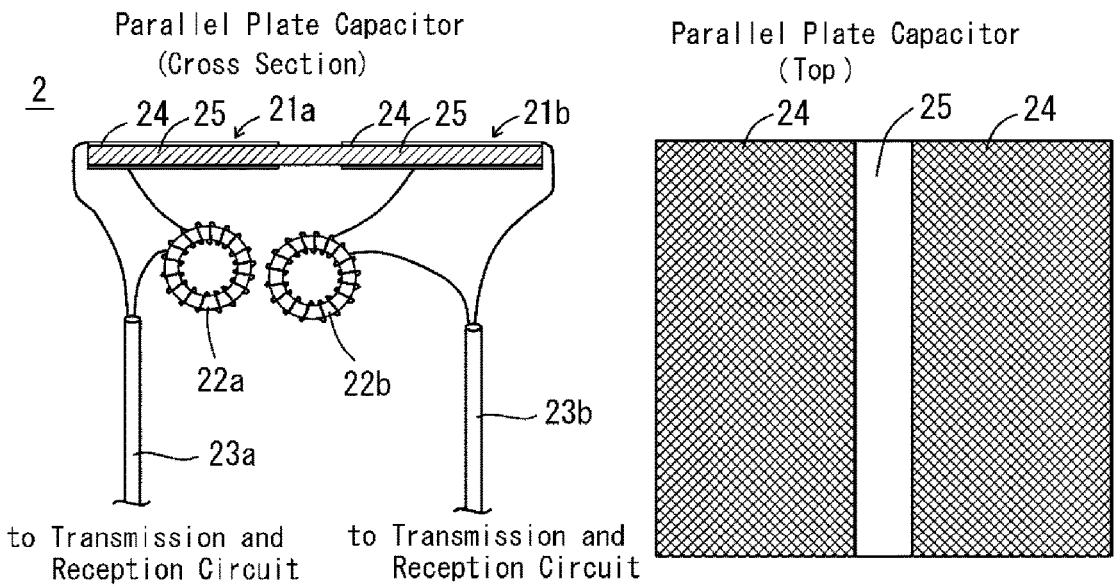
FIG. 2 is a diagram showing an example of configuration of a plural frequency type electric near-field probe.

Next, a plural frequency type electric near-field probe is described below. In the plural frequency type electric near-field probe, two or more parallel plate type capacitors like that described above are employed and then an inductor using a toroidal core is attached independently to each capacitor. FIG. 2 shows outlines of an electric near-field probe having two resonance frequencies (the right part is a top view and the left part is a sectional view).

As an example, an electric near-field probe 2 having two different resonance frequencies is constructed from combinations between a capacitor 21a and an inductor 22a and between a capacitor 21b and an inductor 22b so that two resonance circuits whose resonance frequencies are different are formed. Then, each resonance circuit is connected to the transmission and reception circuit through a coaxial cable 23a or 23b. Here, the resonance frequencies are set suitably into appropriate frequencies in accordance with the application. Here, in FIG. 2, numeral 24 indicates a metal plate fabricated from a copper foil and numeral 25 indicates a dielectric material of polytetrafluoroethylene.

When a plurality of series resonance circuits having different resonance frequencies are provided, as described above, a plurality of piezoelectric crystals having different resonance frequencies depending on the kind, the particle size, or the like can efficiently be detected by using one electric near-field probe.

(3) Gradio Structure Type

Figure 3:
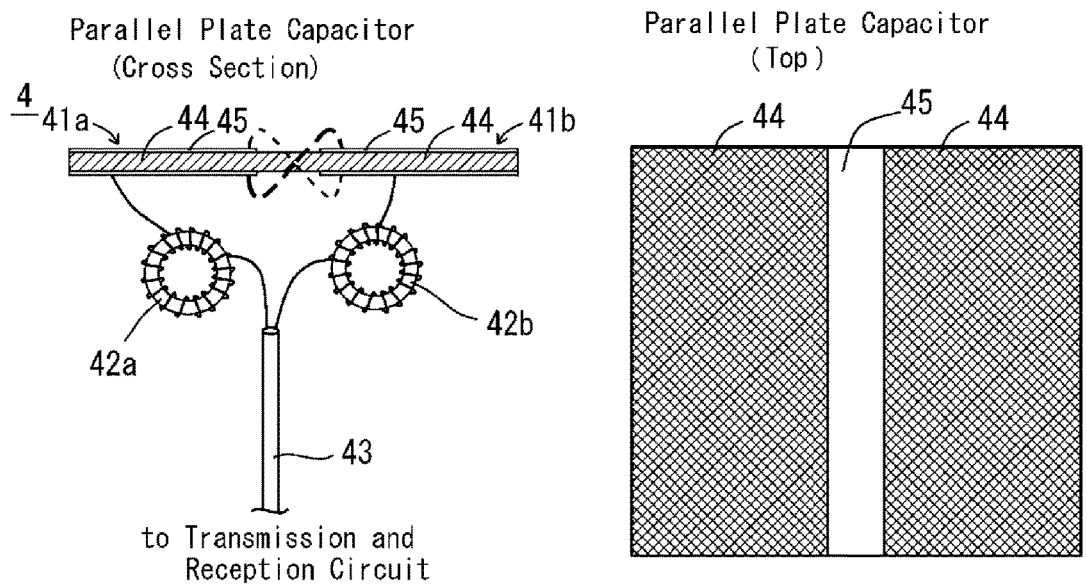
FIG. 3 is a circuit diagram showing an example of configuration of a gradio structure type electric near-field probe.

Next, a gradio structure type electric near-field probe is described below. FIG. 3 shows outlines of a gradio structure type electric near-field probe (the right part is a top view and the left part is a sectional view). In a gradio structure type electric near-field probe 4, capacitors 41a and 41b having the same shape and size are aligned in parallel and then connected in opposite polarity to each other. Specifically, two identical capacitors of parallel plate type are aligned in a plane and then connected such that the relation of connection to the front and the rear surface of each capacitor becomes opposite to each other. By virtue of this, a gradio structure is constructed. Here, in FIG. 3, numeral 43 indicates a coaxial cable, numeral 44 indicates a metal plate fabricated from a copper foil, and numeral 45 indicates a dielectric material of polytetrafluoroethylene.

When the connection is in opposite polarity to each other, leakage electric near-fields from the two capacitors 41a and 41b aligned in parallel are in opposite directions to each other and hence the electric fields cancelled out at a distance. Thus, an electric near-field probe in which the electric field intensity at a distance is attenuated to the regulation value or lower and yet attenuation of the electric field intensity in the vicinity is avoided as much as possible can be provided within the regulation range by Radio Act.

At that time, when an inductor 42a, a capacitor 41a, a capacitor 41b, and an inductor 42b are connected in this order, in the two electrodes of the capacitor, similarly to the above-mentioned single frequency type, the voltages oscillate relative to the ground so that resonance can be obtained.

2. Control System

Next, a basic configuration of a control system for controlling the electric near-field probe is described below.

(1) Single Frequency Control Circuit

Figure 4:
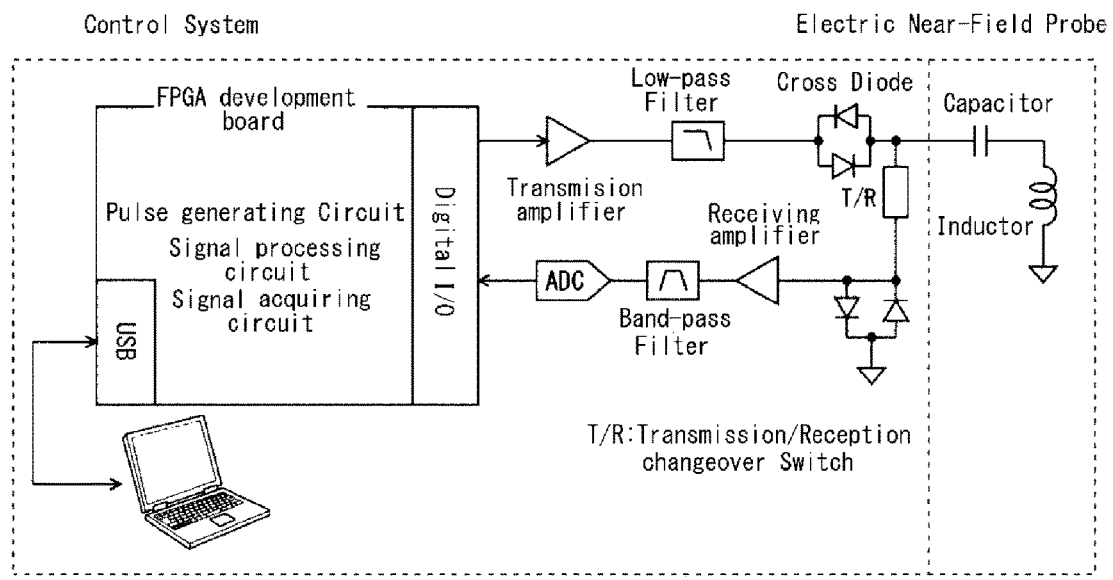
FIG. 4 is a circuit diagram showing an example of configuration of a single frequency type electric near-field probe and a control system for this.

FIG. 4 is a circuit diagram showing an example of configuration of a single frequency type electric near-field probe and a control system for this. A piezoelectric crystal detector is constructed from the electric near-field probe and a circuit (a control circuit) of the control system.

For example, in the control circuit, a commercially available FPGA development board is employed. Then, a pulse generating circuit, a signal processing circuit, and a signal acquiring circuit are constructed in the inside of the FPGA so that the control circuit can be fabricated.

As shown in FIG. 4, a transmission signal is outputted from a digital input/output terminal of the FPGA, then amplified by a transmission amplifier, and then provided through a low-pass filter and a cross diode to the electric near-field probe. At that time, the electric near-field probe, the cross diode, and the transmission amplifier constitute a series resonance circuit.

In association with the voltage amplification by the resonance circuit, the voltage across both ends of the capacitor becomes Q (10 to 150)-fold the output voltage of the transmission amplifier. Thus, the output intensity of the electric near-field can be increased further.

Further, at the time of receiving, a band-pass filter is provided so that an alternating electric field near the resonance frequency of the electric near-field probe is received. This reduces an external noise having a frequency component outside the band.

Here, in order to increase the voltage amplification factor at the time of transmission, it is preferable that a D-class amplifier circuit having a low power consumption within the amplifier and capable of low-impedance output is employed as the transmission amplifier. Then, in association with this, as shown in FIG. 4, it is preferable that a low-pass filter is arranged immediately behind the transmission amplifier so that leakage of radio waves of harmonic components of the excitation frequency from the electric near-field probe including the cable is prevented.

Next, when the cross diode of FIG. 4 is arranged immediately behind the low-pass filter of the series resonance circuit, a transient phenomenon occurring in the electric near-field probe after transmission of a transmission pulse can be reduced. That is, as the voltage acting on the electric near-field probe after transmission attenuates and approaches the forward threshold voltage of the diode, the resistance component of the diode varies nonlinearly in accordance with the applied voltage and thereby increases rapidly. Thus, the energy accumulated in the resonance circuit is efficiently consumed by the resistance of the diode and hence a transient phenomenon can be reduced. Further, also in order that, at the time of receiving, the transmission amplifier of low impedance may be disconnected so that the configuration may be changed into a resonance circuit having a receiving amplifier, the cross diode need be arranged.

Further, in order that the output from the transmission amplifier may be not transferred to the receiving side, a transmission/reception changeover switch constructed from a semiconductor relay or a reed relay may be employed. The cross diode arranged immediately in front of the receiving amplifier is inserted for the purpose of clamping the signal when a large voltage acts on the receiving amplifier.

As the receiving amplifier, one having an amplification factor of approximately 50 to 100 dB is employed. Then, for the purpose of reducing a subsequent noise and preventing aliasing in an ADC, a band-pass filter or a low-pass filter is employed.

The output of the ADC is transferred from the digital input/output terminal to the FPGA and then, in the inside, lead to a circuit for accumulating the piezoelectric effect signal and an FFT circuit for calculating a frequency spectrum.

When a high-speed ADC (10 to 100 MHz) of parallel type is employed as the ADC, in the inside of the FPGA, phase detection is performed on the output signal of the ADC so that the signal is decomposed into two components whose phases are different by 90 degrees and then measurement is performed.

Further, when a low-speed ADC (1 to 3 MHz) of serial type is employed, the sampling frequency is set to be 4/(odd number)-fold the excitation frequency so that the signal can be decomposed into two components whose phases are different by 90 degrees by a band-pass sampling method.

The transmission frequency, the pulse width, the repeat time, and the data receiving time can be controlled through software constructed onto a PC through a USB. Further, when information such as the transmission frequency, the pulse width, the repeat time, and the data receiving time is set up in advance as initial values on the FPGA, the system can be controlled also in a PC-free manner.

(2) Control Circuit for Plural Frequency

Figure 5:
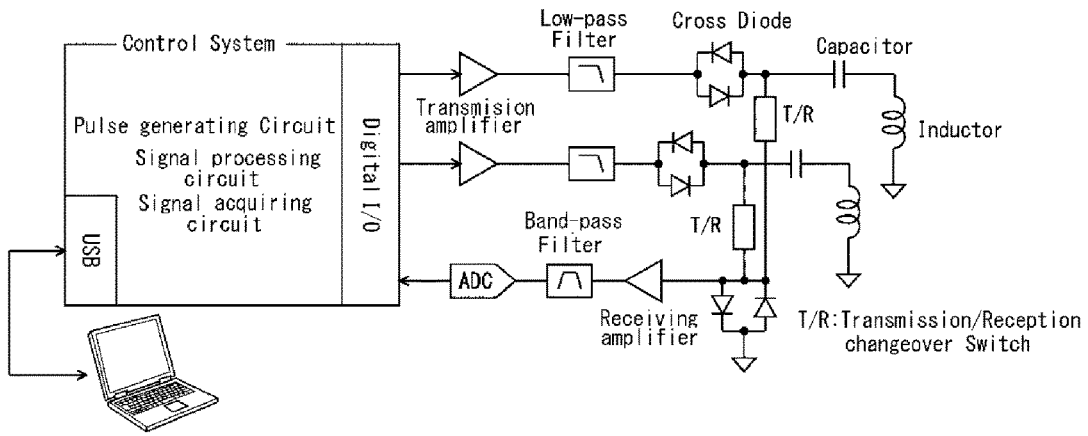
FIG. 5 is a circuit diagram showing an example of configuration of a plural frequency type electric near-field probe and a control system for this.
Figure 6:
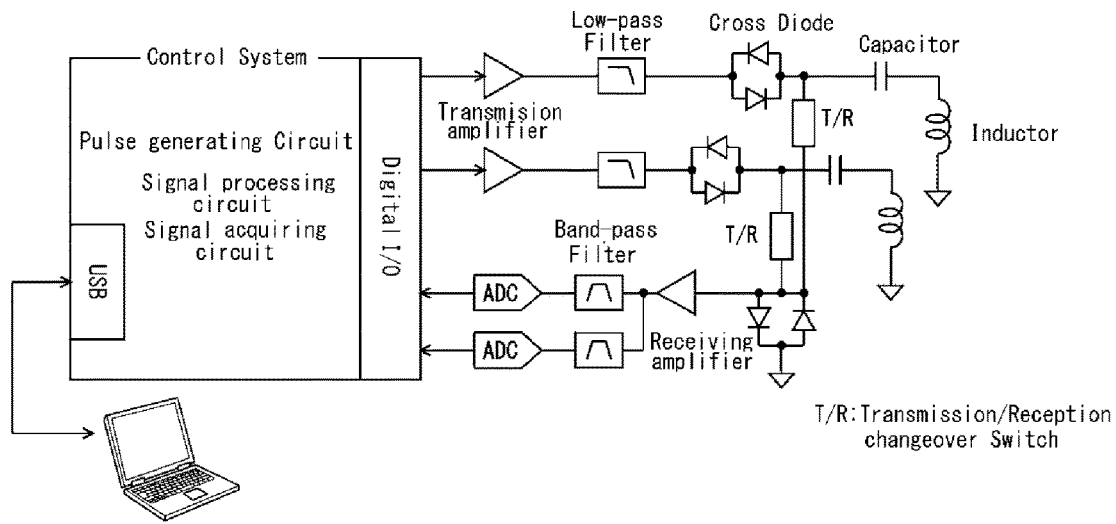
FIG. 6 is a circuit diagram showing another example of configuration of a plural frequency type electric near-field probe and a control system for this.
Figure 7:
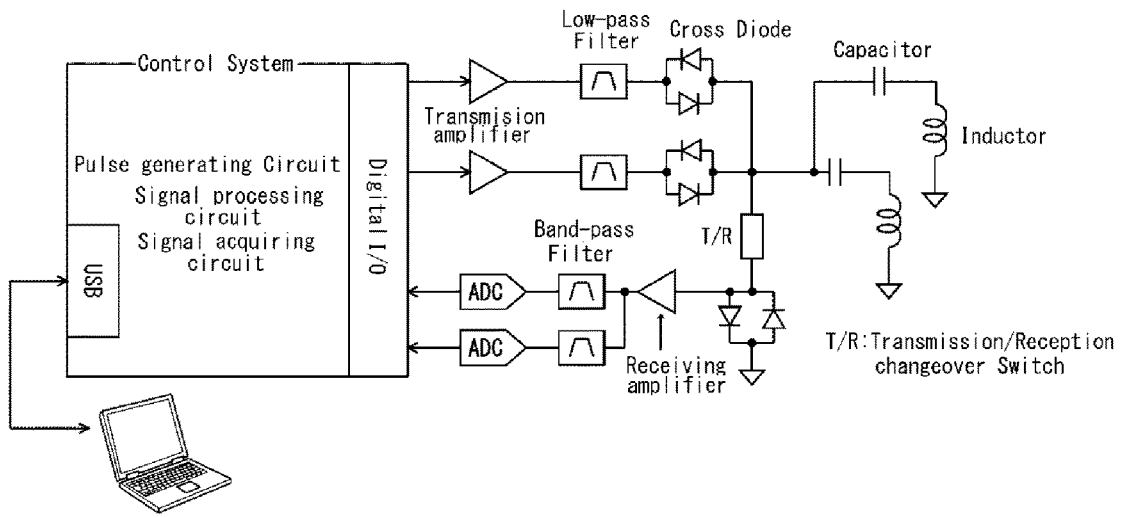
FIG. 7 is a circuit diagram showing another example of configuration of a plural frequency type electric near-field probe and a control system for this.

Each of FIGS. 5 to 7 is a circuit diagram showing a configuration example of a plural frequency type of an electric near-field probe and a control system for this. Since excitation pulse signals of a plurality of frequencies need simultaneously be transmitted, a plurality of transmission amplifiers are provided. This is the difference point from the control circuit for single frequency shown in FIG. 4.

At that time, when the frequencies of transmission are close, that is, in a case that the plurality of frequencies fall within the bandwidth of the band-pass filter, as shown in FIG. 5, the piezoelectric effect signal can be received by using one band-pass filter and ADC arranged immediately behind the receiving amplifier.

On the other hand, when the frequencies of transmission are separate largely, that is, in a case that the plurality of frequencies fall outside the bandwidth of the band-pass filter, as shown in FIG. 6, a plurality of band-pass filters having different center frequencies suitable for each are arranged immediately behind the receiving amplifier and then each piezoelectric effect signal is received by each separate ADC.

Further, as shown in FIG. 7, in a case that a band-pass filter is employed in place of the low-pass filter arranged behind the transmission amplifier, the coaxial cables connecting the electric near-field probes and the transmission and reception circuits can be collected into one.

(3) Control Circuit for High-Sensitivity Receiving

When the electric near-field probe is used in an electromagnetic field shield environment, a noise from the outside is reduced. Thus, when a noise from the reception circuit is reduced, the receiving sensitivity for the piezoelectric effect signal can be increased. Nevertheless, when the receiving amplifier is inserted in series to the series resonance circuit, a problem is caused that a noise originating from the receiving amplifier becomes dominant over a thermal noise occurring from the resistance contained in the electric near-field probe.

Figure 8:
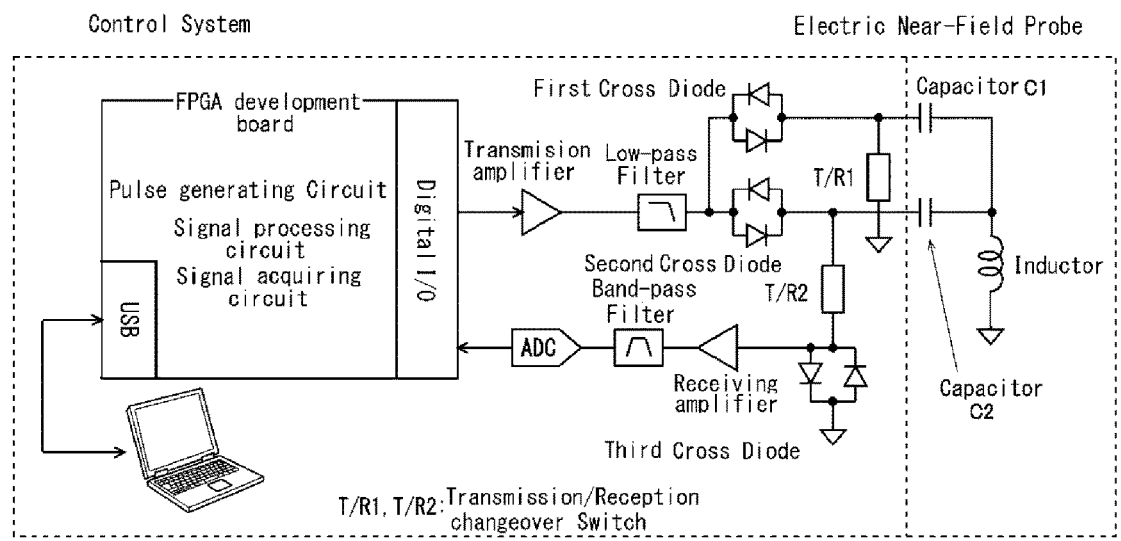
FIG. 8 is a circuit diagram showing an example of configuration of a high-sensitivity receiving type electric near-field probe and a control system for this.

In order to resolve this problem, it is preferable to employ a control circuit for high-sensitive receiving in which the configuration of the resonance circuit is switched between transmission and receiving as shown in FIG. 8.

FIG. 8 is a circuit diagram showing an example of configuration of a high-sensitivity receiving type electric near-field probe and a control system for this. As shown in FIG. 8, the electric near-field probe contains a series resonance circuit constructed such that terminals of the capacitor C1 and the capacitor C2 connected in parallel are connected together to one inductor. Then, the transmission amplifier is connected through the first cross diode to the other terminal of the capacitor C1 and, at the same time, connected through the second cross diode to the other terminal of the capacitor C2.

Further, the first cross diode and the other terminal of the capacitor C1 are connected to one terminal of a first transmission/reception changeover switch (T/R1) and then the second cross diode and the other terminal of the capacitor C2 are connected to one terminal of a second transmission/reception changeover switch (T/R2). The other terminal of the first transmission/reception changeover switch (T/R1) is connected to the ground.

Further, the receiving amplifier is connected to the other terminal of the second transmission/reception changeover switch (T/R2) and the other terminal of the second transmission/reception changeover switch (T/R2) is connected to the ground through the third cross diode.

At the time of transmission, the first cross diode and the second cross diode are brought into conduction so that the transmission amplifier is connected to the other terminal of the capacitor C1 and the other terminal of the capacitor C2 and, at the same time, the first transmission/reception changeover switch (T/R1) and the second transmission/reception changeover switch (T/R2) are shut off so that the receiving amplifier is disconnected.

At the time of receiving, the transmission amplifier is disconnected by the first cross diode and the second cross diode and, at the same time, the first transmission/reception changeover switch (T/R1) and the second transmission/reception changeover switch (T/R2) are brought into conduction so that the receiving amplifier is connected to the other terminal of the capacitor C2.

As such, at the time of transmission, the first cross diode and the second cross diode are brought into conduction so that the transmission amplifier is connected in series to the electric near-field probe and, at the same time, the first transmission/reception changeover switch (T/R1) and the second transmission/reception changeover switch (T/R2) are shut off so that the receiving amplifier is disconnected. On the other hand, at the time of receiving, the transmission amplifier is disconnected by the first cross diode and the second cross diode and, at the same time, the first transmission/reception changeover switch (T/R1) and the second transmission/reception changeover switch (T/R2) are brought into conduction so that the receiving amplifier is connected in series to the electric near-field probe.

When the control circuit has the above-mentioned configuration, at the time of transmission, the noise source of the amplifier and the noise source of the electric near-field probe are both connected to the capacitors C2 and C1 in series. Thus, the amplification factor for the noise becomes the same in the amplifier and in the electric near-field probe. On the other hand, at the time of receiving, the noise source from the receiving amplifier is inserted in series to the capacitor C2 and the noise source from the electric near-field probe is connected in series to both capacitors C2 and C1. By virtue of this, the amplification factor for the noise generated by the receiving amplifier and the amplification factor for the signal generated from the electric near-field probe can be varied. Thus, when optimal values are employed, the receiving sensitivity can be improved.

(4) Pulse Sequence a. Single Frequency Pulse Sequence

As described above, in order that a piezoelectric effect signal may be generated from a piezoelectric crystal, an alternating electric field corresponded to the mechanical resonance frequency specific to each crystal need be applied. Nevertheless, the piezoelectric effect signal is extremely weaker than the alternating electric field for excitation.

Figure 9:
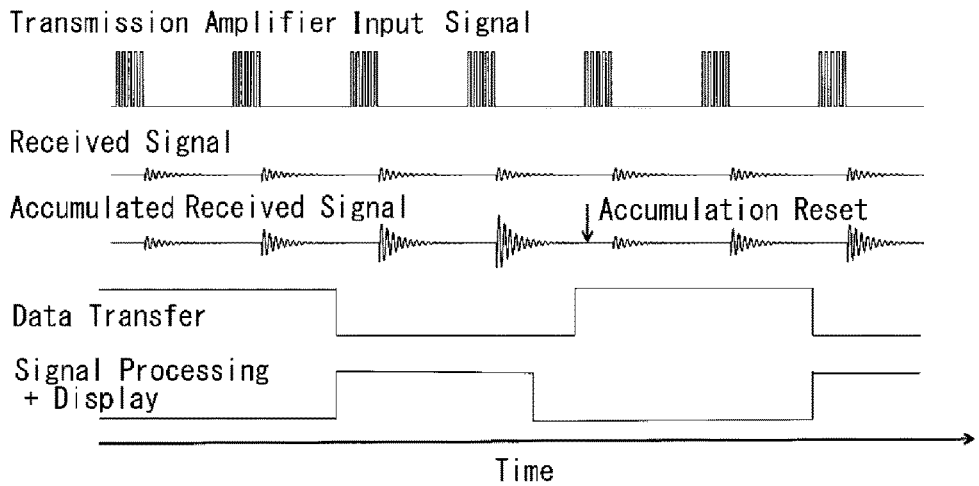
FIG. 9 is a diagram describing an example of a pulse sequence for single frequency.

Thus, at the time of measurement, transmission and reception are alternately performed and then, at the time of receiving, transmission of the alternating electric field is stopped. After that, the piezoelectric effect signal generated from the crystal vibrating with time decay is received. Usually, the decay time is approximately 1 ms or shorter. Then, when the piezoelectric effect signal has attenuated to a certain extent, as shown in FIG. 9, an alternating electric field for transmission is applied again so as to excite the piezoelectric crystal and then the piezoelectric effect signal is received. Then, these processes are repeated.

At that time, in a case that the phase of the transmitted alternating electric field is reset at each time so that transmission is always performed with the same phase, the phases of the received signals become the same and hence accumulation of the weak piezoelectric effect signals is allowed. The number of accumulation times can be set up arbitrarily. Nevertheless, a larger number of accumulation times causes more delay in the cycle until the result is displayed. Thus, it is preferable that the total accumulation time is set to be several hundred ms.

In the present invention, an object is to detect a piezoelectric crystal in real time. Thus, frequency analysis is performed on the accumulated received signal so that the presence or absence of a piezoelectric effect signal is tested. After accumulation, the received signal is reset and then accumulation is performed again. Further, in a case that processing of the previous accumulation data is performed in parallel during the next accumulation, dead time in the measuring time caused by the data processing and test can be avoided.

b. Pulse Sequence for Plural Frequency

Figure 10:
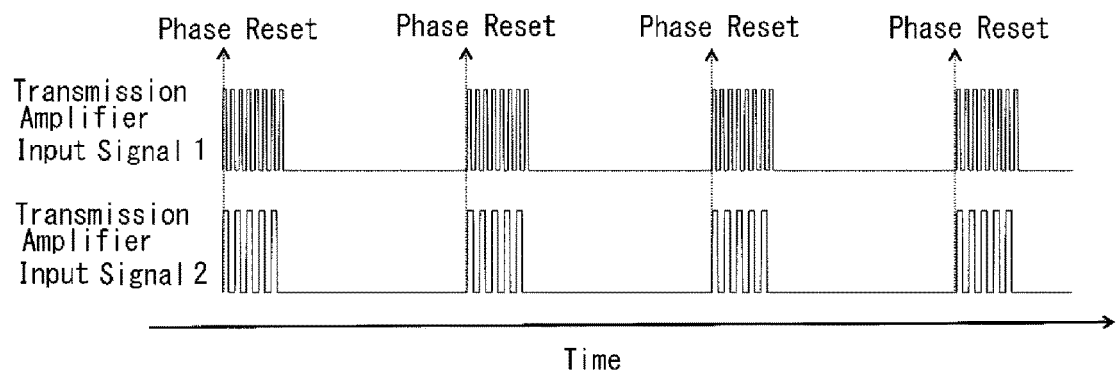
FIG. 10 is a diagram describing an example of a pulse sequence for plural frequency.

In order that a plurality of piezoelectric crystals having different resonance frequencies may simultaneously be excited, as described above, alternating electric fields containing a plurality of frequency components need simultaneously be transmitted. In such a case, according to a sequence shown in FIG. 10, the transmission time and the transmission interval are set identical in the alternating electric fields containing a plurality of frequency components and then piezoelectric effect signals having different frequencies are received after the transmission of the alternating electric fields. Further, in a case that the phases are reset at each time when the alternating electric fields having different frequencies are transmitted, accumulation is allowed to be performed on each of the piezoelectric effect signals acquired simultaneously.

c. Frequency-Modulated Pulse Sequence

Figure 11:
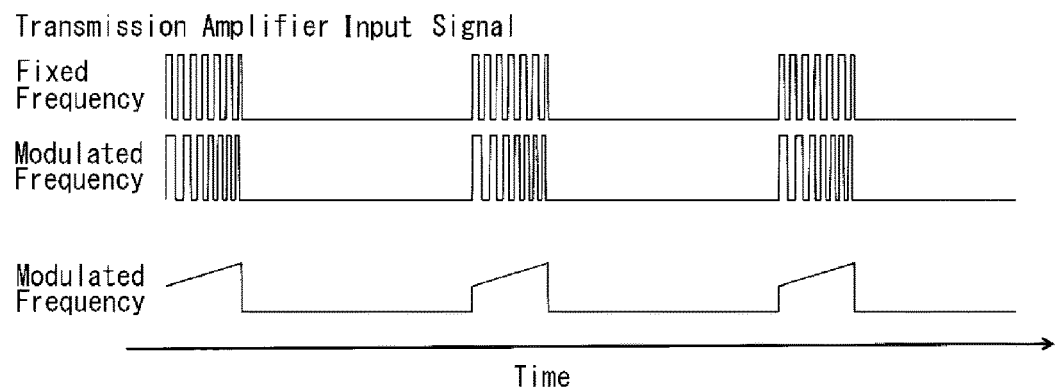
FIG. 11 is a schematic diagram of a frequency-modulated pulse sequence.

In order that a plurality of piezoelectric crystals having different resonance frequencies may simultaneously be excited, according to a sequence shown in FIG. 11, the frequency of the transmission signal may be modulated. Also in this case, when the phase is reset at each time in the transmission signal, accumulation of the piezoelectric effect signal is allowed. However, it is preferred that the frequency modulation width is set up within the band of the probe.

(5) Transmission Amplifier

When a sine burst wave (a wave obtained by pulse modulation on the intensity of a continuous sine wave) is inputted to the resonance circuit, a delay having a time constant $t=Q/(\pi f)$ (here, f is the frequency of the modulated wave) depending on the Q characteristics of the resonance circuit occurs in the rise and the fall in the voltage and the electric current of the resonance circuit. Thus, in some cases, a weak signal generated from a piezoelectric substance is hidden by the transmission signal at the time of fall so that the start time of detection is delayed. When the start time of detection is delayed as such, the piezoelectric effect signal attenuates exponentially with respect to time so that degradation is caused in the receiving sensitivity for the piezoelectric effect signal.

Figure 12:
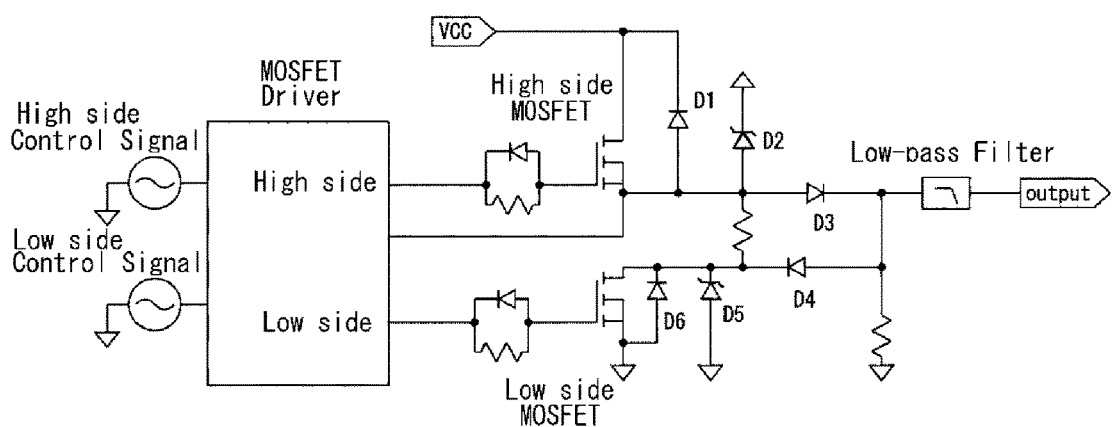
FIG. 12 is a circuit diagram showing an example of configuration of a transmission amplifier.

Thus, an improved D-class amplifier for transmission shown in FIG. 12 is employed so that the above-mentioned fall time is to be reduced.

As shown in FIG. 12, similarly to a D-class amplifier of half bridge type or full bridge type according to the conventional art, in the improved D-class amplifier for transmission, a MOSFET is provided on each of the high side and the low side. However, in contrast to the conventional configuration that the source terminal of the MOSFET on the high side and the drain terminal of the MOSFET on the low side are directly connected, two diodes D3 and D4 are arranged in the middle thereof.

By virtue of this, the direction of the electric current switched by the MOSFET can be made in one direction. Thus, when the control signal becomes a low level signal, the electric current of the series resonance circuit connected to the output can be controlled to be one direction and hence the resonance can be terminated in several cycles so that the fall time can be reduced.

Here, an improved D-class amplifier having a half bridge type configuration has been shown in FIG. 12. Instead, a D-class amplifier having a full bridge type configuration may similarly be constructed.

Figure 13:
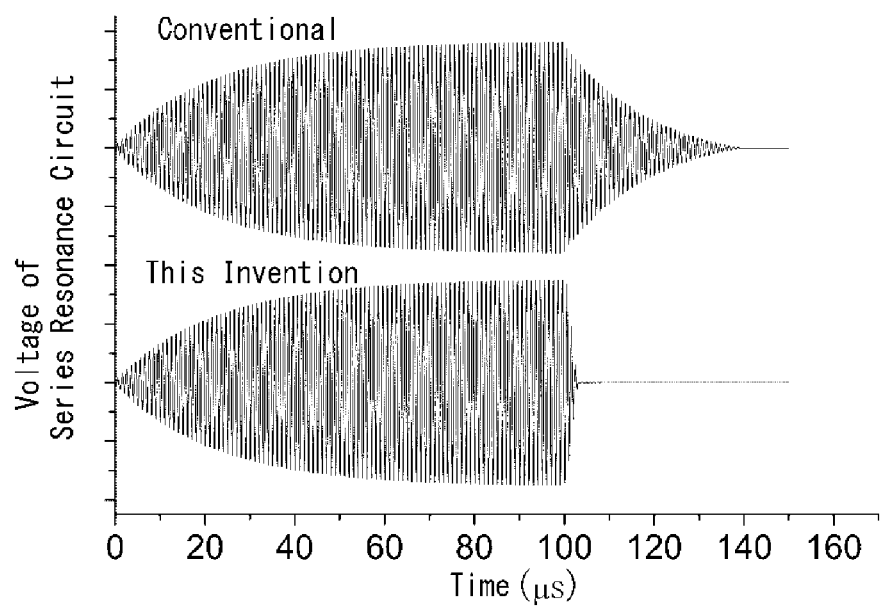
FIG. 13 is a diagram showing a voltage waveform of a sine burst wave generated in a resonance circuit by using a transmission amplifier shown in FIG. 12.

FIG. 13 shows the voltage waveform generated in the electric near-field probe employing the improved D-class amplifier, that is, the voltage waveform of a transmission sine burst wave generated in the resonance circuit, together with that of a case that a D-class amplifier of the conventional art is employed. Here, in FIG. 13, the vertical axis indicates the voltage of the series resonance circuit and the horizontal axis indicates time (µs). From FIG. 13, it is recognized that when the D-class amplifier is employed, the fall time of the alternating electric field is reduced.

3. Piezoelectric Crystal Detector

Figure 14:
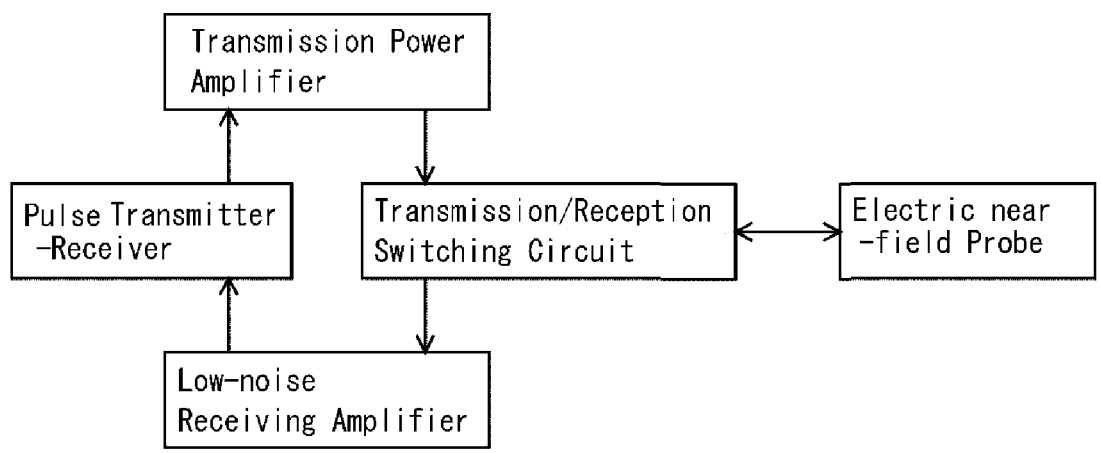
FIG. 14 is a block diagram showing a configuration of a piezoelectric crystal detector according to an embodiment of the present invention.
Figure 15:
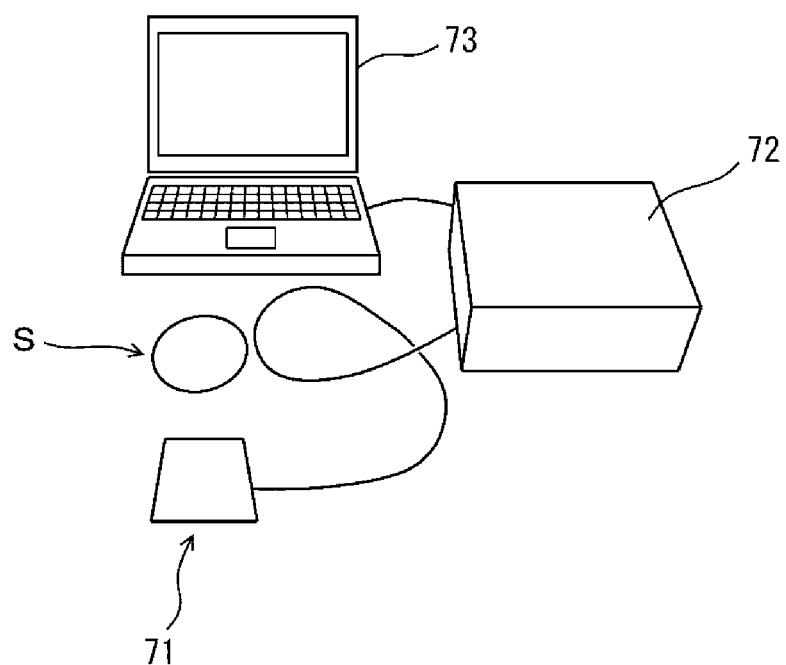
FIG. 15 is a perspective view of a piezoelectric crystal detector according to an embodiment of the present invention.

Next, a piezoelectric crystal detector is described below that contains the electric near-field probe and the control system described above. FIG. 14 is a block diagram showing the configuration of a piezoelectric crystal detector according to the present embodiment. FIG. 15 is a perspective view of the piezoelectric crystal detector according to the present embodiment.

As shown in FIG. 14, the piezoelectric crystal detector of the present embodiment has: a control circuit constructed from a transmission power amplifier, a pulse transmitter-receiver, a low-noise receiving amplifier, and a transmission/reception switching circuit; and an electric near-field probe.

Specifically, as shown in FIG. 15, a control system 72 including the above-mentioned control circuits is connected to the above-mentioned electric near-field probe 71 and a personal computer 73 for displaying the measurement result on a display, so that a piezoelectric crystal detector 7 is constructed. Symbol S indicates an object to be inspected in inspection concerning the presence or absence of a piezoelectric crystal.

Here, the measurement result need not be indispensably displayed on the display and, for example, warning may be issued by employing an alarm composed of sound or light.

In the piezoelectric crystal detector 7 according to the present embodiment, when the small electric near-field probe 71 is merely held over the inspection object S in the vicinity, a piezoelectric effect signal can be received with a sufficient intensity so that inspection can be achieved with high accuracy. Further, since size reduction also can be achieved in the control system 72, size and weight reduction can sufficiently be achieved in the entirety of the piezoelectric crystal detector 7.

Here, in a case that inspection is performed by using the above-mentioned piezoelectric crystal detector, when an electrically conductive material such as a human body and a large metal is present in the vicinity, a change is caused in the resonance frequency so that an external noise not originating from the piezoelectric effect occurs and thereby, in some cases, causes difficulty in detection of a piezoelectric crystal.

Thus, it is preferable that the change in the resonance frequency is detected in advance so that degradation in the inspection accuracy is suppressed.

4. Application of Piezoelectric Crystal Detector

Next, a detailed application of the piezoelectric crystal detector according to the present embodiment is described below.

(1) Detection of Piezoelectric Crystal of Illicit Drug

The present inventor has found a frequency band resulting enough detection efficiency for the detection of illicit drugs such as stimulant. Thus, when a handy type electric near-field probe is merely held over an object, a piezoelectric effect signal can be acquired with sufficient detection sensitivity. Accordingly, when the piezoelectric crystal detector of the present embodiment is used as an illicit drug detector, a prominent effect is expected to be obtained in detection of illicit drugs such as stimulant.

Further, when the frequency band is suitably changed, the apparatus can effectively be used also in detection of piezoelectric crystals other than illicit drugs.

(2) Non-Contact Key System

A non-contact key system in which an object provided with a piezoelectric crystal buried therein is employed as a key and then, when the object is held over a piezoelectric crystal detector so that transmission and reception are performed between the key and the piezoelectric crystal detector, the authentication and unlocking are achieved with high security performance. Hence, this non-contact key system is preferable.

5. Electric Field Intensity Around Electric Near-Field Probe

Next, the electric field intensity generated around the electric near-field probe of the present embodiment is described below.

Figure 16:
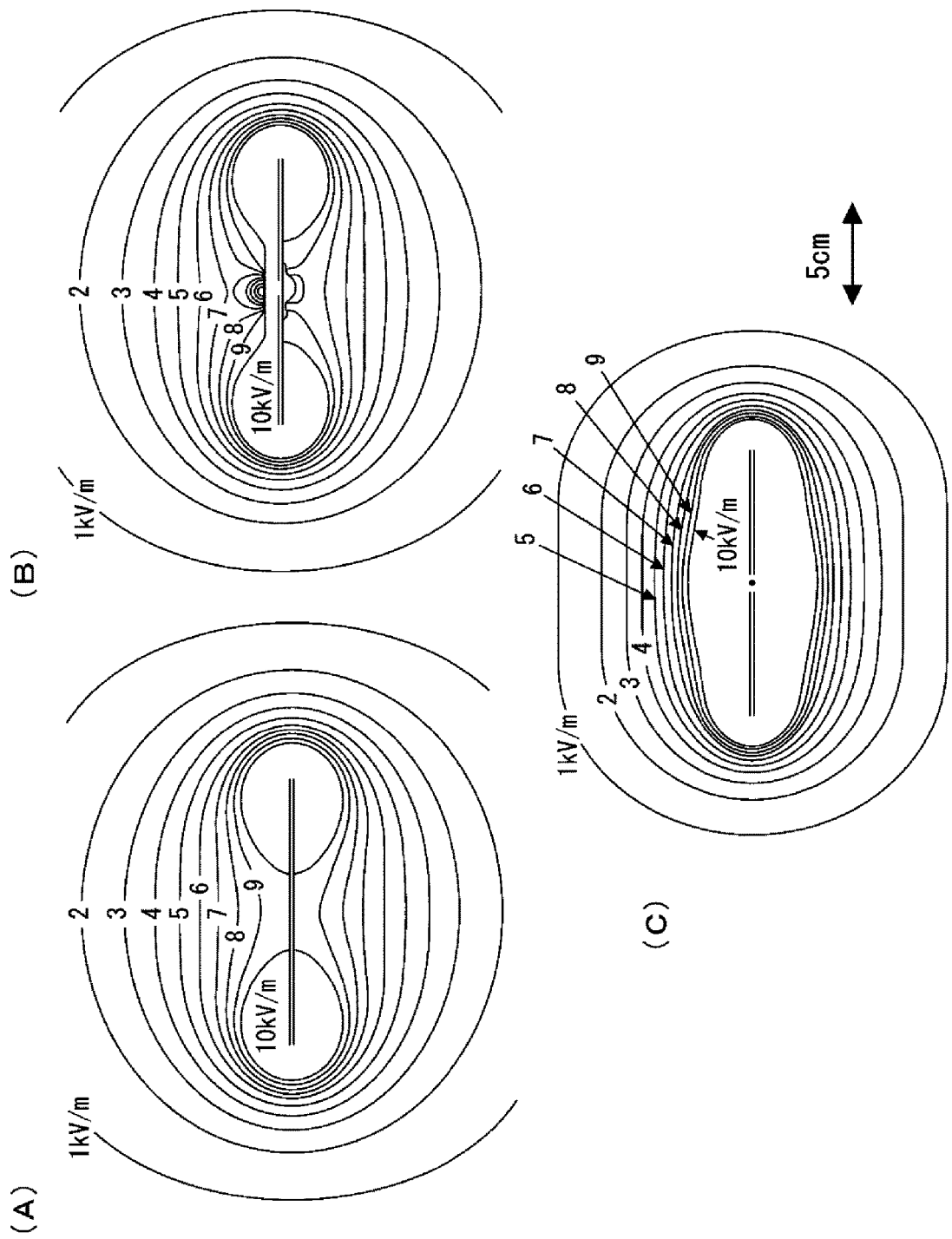
FIG. 16 is a diagram showing electric field intensity generated in the vicinity of a capacitor of an electric near-field probe.

FIG. 16 shows the electric field intensities generated around a single frequency electric near-field probe (A), a single frequency electric near-field probe (B) having an opening part provided in the upper face center part of a metal plate, and a gradio structure type electric near-field probe (C). Here, FIG. 16 shows results obtained when a premised situation that a high frequency of 1000 V as instantaneous amplitude is applied on a parallel plate capacitor used in each electric near-field probe is calculated by employing a three-dimensional electromagnetic field analysis simulator (FEKO) fabricated by EMSS. Two horizontal parallel lines in the center indicate the capacitor.

From FIG. 16, it is recognized that an electric field is generated around the electric near-field probe. Then, it is recognized that in the single frequency electric near-field probe having an opening part provided in the upper face center part of a metal plate, the electric field intensity is high especially above the upper face center part of the metal plate. Further, it is recognized that in the gradio structure type electric near-field probe, sufficient electric field intensity is maintained in the vicinity and yet the electric field intensity is reduced at a position away from the capacitor.

6. Transmission Waveform from Electric Near-Field Probe

Next, the waveform transmitted from the electric near-field probe is described below. When a transmission amplifier input signal is inputted to the transmission amplifier and then the output voltage is applied to the electric near-field probe, an alternating electric field is generated from the electric near-field probe.

(1) Single Frequency Type

Figure 17:
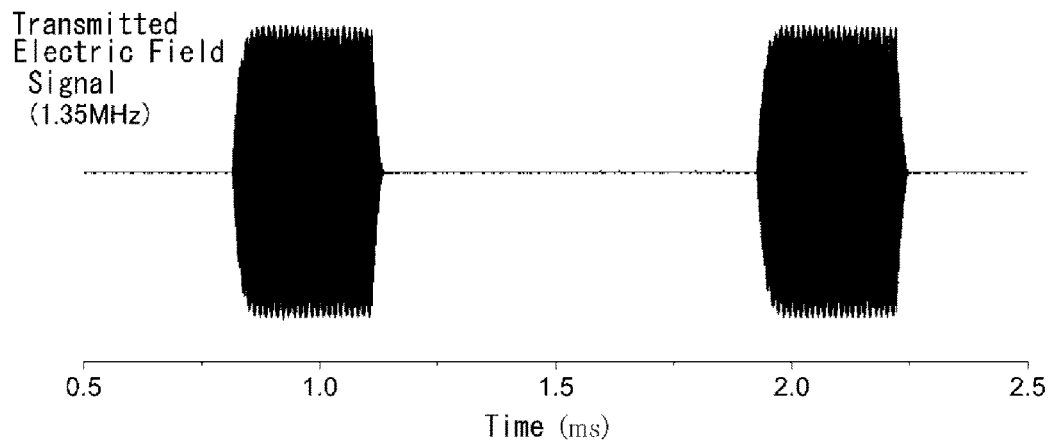
FIG. 17 is a waveform obtained when a waveform of an excitation transmission pulse (a sine burst wave) from an electric near-field probe is received by an electric field probe installed in the vicinity of an electric near-field probe.

FIG. 17 shows a transmission waveform in a case that a 1.35-MHz alternating electric field signal is transmitted as a transmitted electric field signal by using a single frequency type electric near-field probe. Here, this is the waveform of an excitation transmission pulse (a sine burst wave) received by another electric field probe installed in the vicinity of the electric near-field probe.

From FIG. 17, it is recognized that the rise and the fall time are moderated by the Q (quality factor) characteristics of the probe. At that time, a voltage equal to Q-fold the input voltage to the electric near-field probe acts on the capacitor of parallel plate type. Thus, when resonance is utilized, the electric field can efficiently be generated.

(2) Plural Frequency Type

Figure 18:
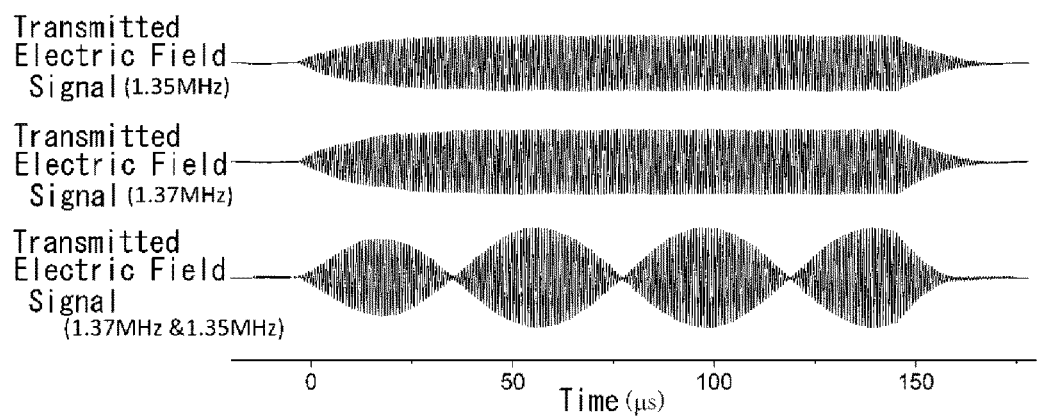
FIG. 18 is a diagram showing an example of a waveform of a transmission pulse in a case that two different excitation transmission pulses (sine burst waves) are transmitted simultaneously.

FIG. 18 shows a transmission waveform in a case that alternating electric field signals having two different frequencies (1.35 MHz and 1.37 MHz) are simultaneously transmitted as transmitted electric field signals by using a plural frequency type electric near-field probe.

From FIG. 18, it is recognized that when simultaneous transmission is performed, waveforms each transmitted independently are added up and then transmitted.

Figure 19:
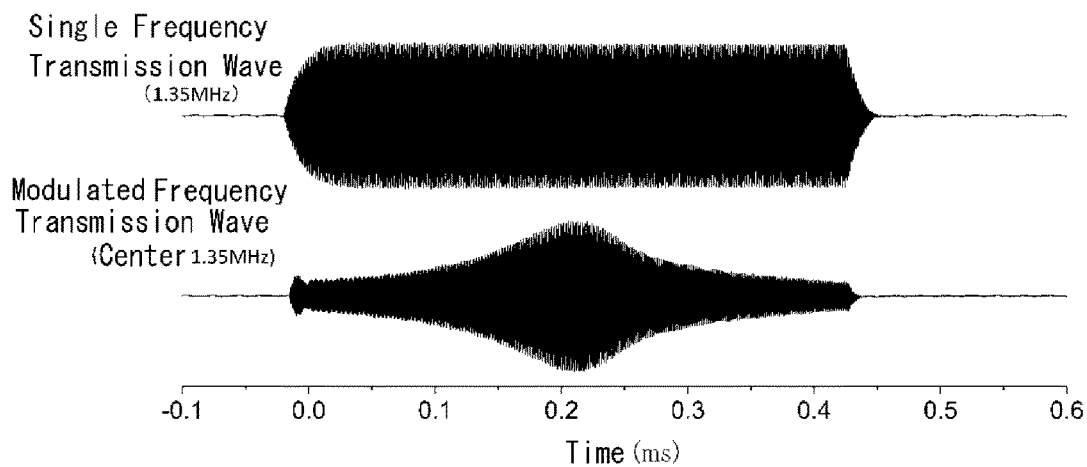
FIG. 19 is a diagram showing an example of a waveform of a modulated transmission pulse (a sine burst wave) having undergone frequency modulation.

As described above, in the plural frequency type electric near-field probe, a signal of sine burst wave obtained by linearly modulating the frequency may also be employed as the transmission amplifier input signal. FIG. 19 shows a transmission waveform in a case that a 1.35-MHz single frequency transmission wave and a modulated frequency transmission wave having a center frequency of 1.35 MHz are simultaneously transmitted.

From FIG. 19, it is recognized that the voltage amplification factor is high at the resonance frequency and hence the generated electric field intensity becomes the maximum. On the other hand, when the frequency of the transmission wave is fixed at the resonance frequency, the voltage amplification factor becomes fixed.

(3) Transmission from Gradio Structure Probe

As described above, when the electric near-field probe is used in the outside of an electromagnetic shield, the electric field intensity at a 30-m away position need to be 100 µV/m or lower.

Figure 20:
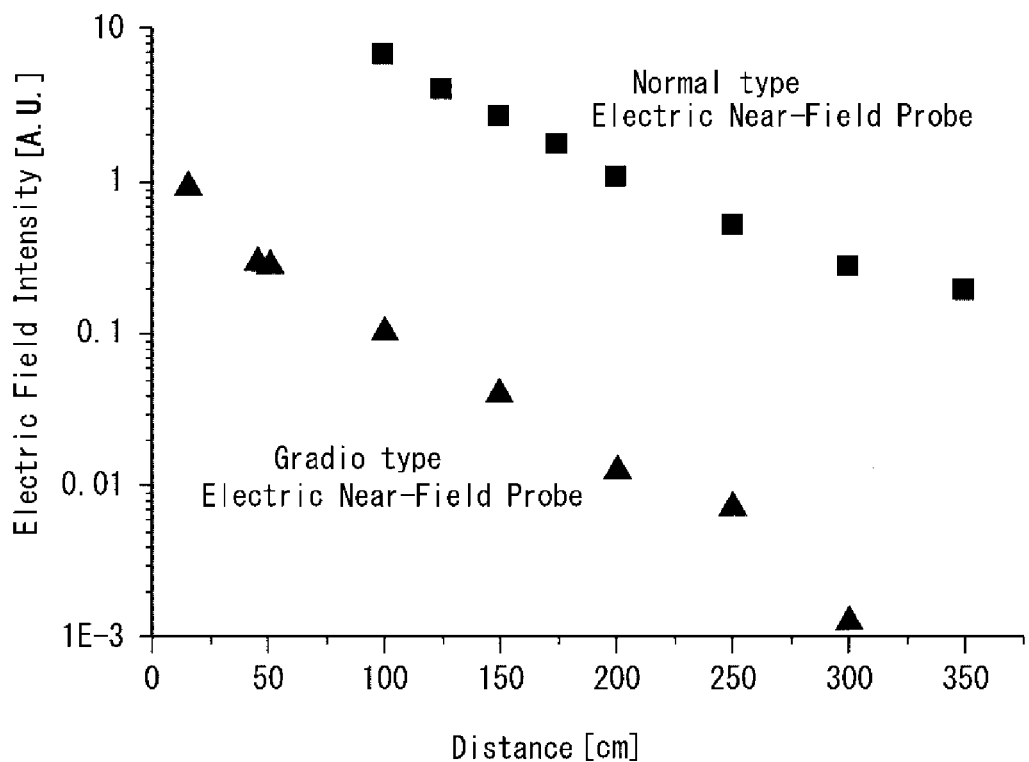
FIG. 20 is a diagram showing an example of measurement results of a relation between electric field intensity and an electric near-field probe.

FIG. 20 shows the results of the electric field intensity generated from a gradio structure type electric near-field probe or an electric near-field probe (a normal type electric near-field probe) constructed from one set of parallel plates (here, the transmission voltage from the transmission amplifier was fixed to 18 V), which was measured with changing the distance from the electric near-field probe. Here, in FIG. 20, the vertical axis indicates the electric field intensity and the horizontal axis indicates the distance from the electric near-field probe.

From FIG. 20, it is recognized that in the case of the gradio structure type electric near-field probe, the electric field intensity is attenuated by approximately 1/10 to 1/50 at a distant place (a distance of 50 cm or greater) from the electric near-field probe.

7. Receiving from Electric Near-Field Probe

Next, receiving from the electric near-field probe, which indicates a piezoelectric effect signal, is described below.

(1) Piezoelectric Crystal and Resonance Frequency

Figure 21:
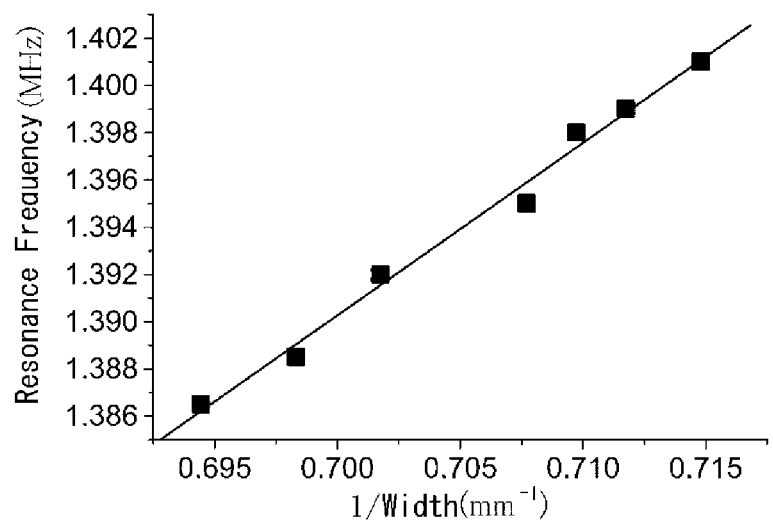
FIG. 21 is a diagram showing a relation between the frequency of a piezoelectric effect signal and the size (the width) of synthetic quartz.

For the purpose of sensing a piezoelectric crystal, an approximate relation between the size of the detected crystal and the applied frequency of an alternating electric field need be investigated in advance. FIG. 21 shows the results of a change in the frequency (the resonance frequency) of a piezoelectric effect signal measured with changing the width of the synthetic quartz. Here, in FIG. 21, the horizontal axis indicates the inverse of the width.

From FIG. 21, it is recognized that the resonance frequency is inversely proportional to the width of the crystal (proportional to the inverse of the width).

Figure 22:
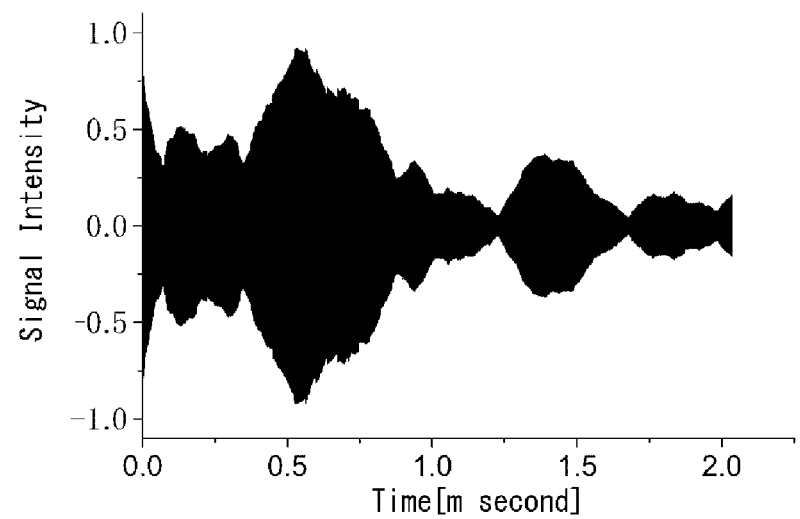
FIG. 22 is a diagram showing a time domain signal (before phase detection) of a piezoelectric effect signal from a plurality of Rochelle crystals.
Figure 23:
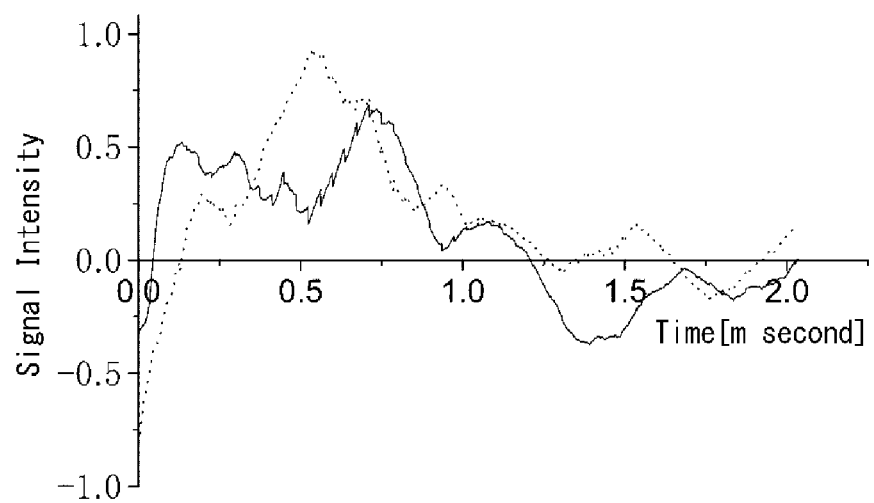
FIG. 23 is a diagram showing a time domain signal (after phase detection) of a piezoelectric effect signal from a plurality of Rochelle crystals.
Figure 24:
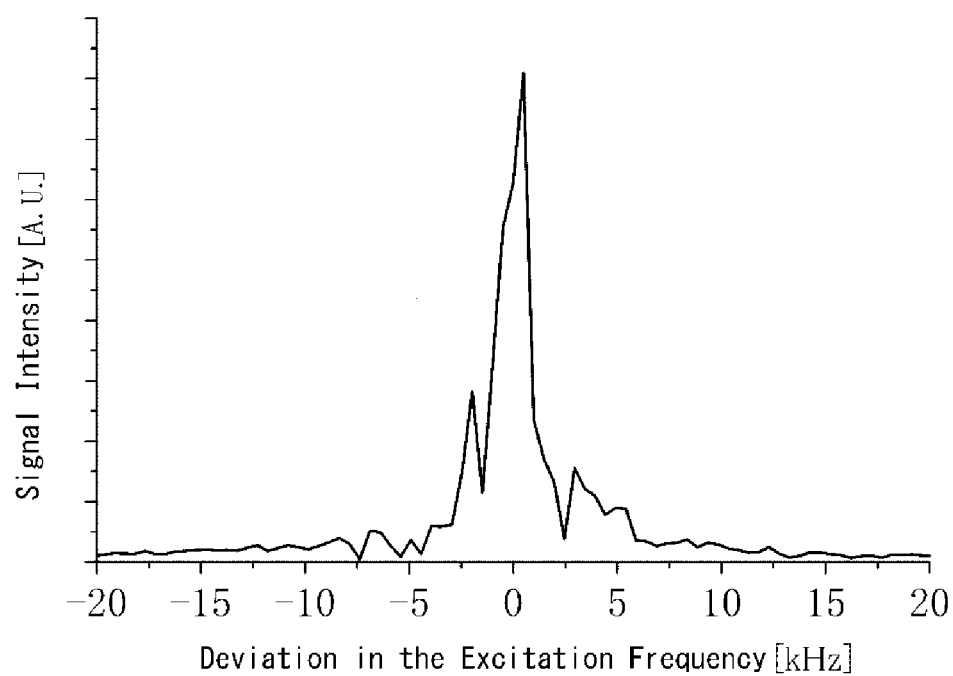
FIG. 24 is a diagram showing a frequency domain signal of a piezoelectric effect signal from a plurality of Rochelle crystals.

In ordinary objects of sensing, piezoelectric crystals having various sizes are expected to be present. However, a piezoelectric effect signal is returned only from crystals having the same resonance frequency as the frequency of the applied alternating electric field. FIGS. 22 to 24 show the results of the piezoelectric effect signal measured for a large number of particles of Rochelle salt crystal having a grain diameter of 5 mm or smaller. FIGS. 22 and 23 show the results of the time domain signal of the piezoelectric effect signal, corresponding before and after phase detections, respectively. Further, FIG. 24 is a diagram showing the signal in the frequency domain of the piezoelectric effect signal.

From FIGS. 22 to 24, it is recognized that when piezoelectric crystals having a plurality of grain diameters are present, a piezoelectric effect signal containing a plurality of frequency components is measured.

(2) Receiving by Excitation using Plural Frequency

Figure 25:
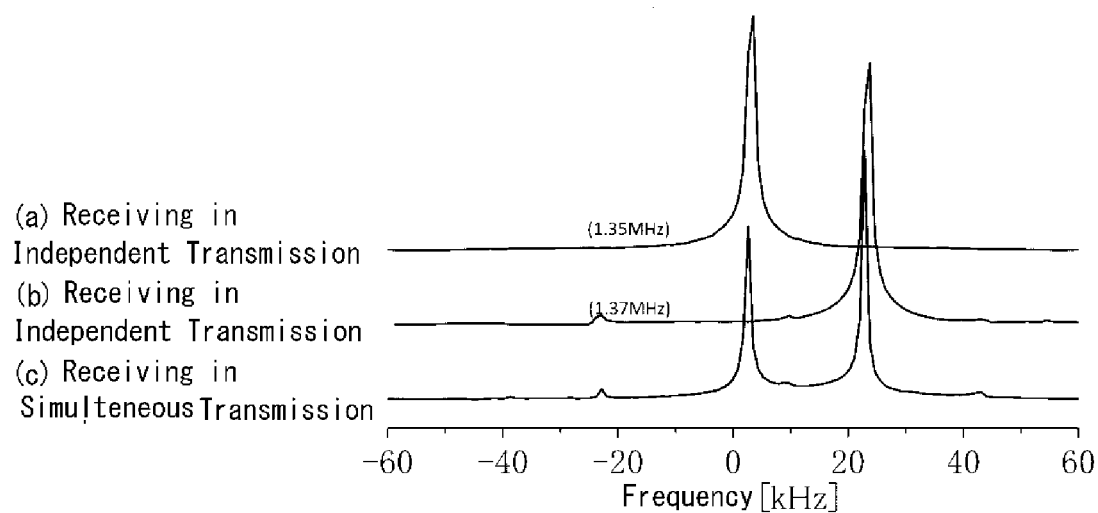
FIG. 25 is a diagram showing a piezoelectric effect signal received from two Rochelle salts having different resonance frequencies by an electric near-field probe having two resonance frequencies.

FIG. 25 shows the results of the frequency spectrum of the piezoelectric effect signal received by the electric near-field probe measured when the electric near-field probe having two resonance frequencies shown in FIG. 2 was brought close to Rochelle salt crystals resonating at two different resonance frequencies.

From FIG. 25, it is recognized that two piezoelectric effect signals each obtained at the time of independent transmission are simultaneously received and that when the two different frequencies are simultaneously transmitted, the piezoelectric effect signal can be received from two crystals.

Figure 26:
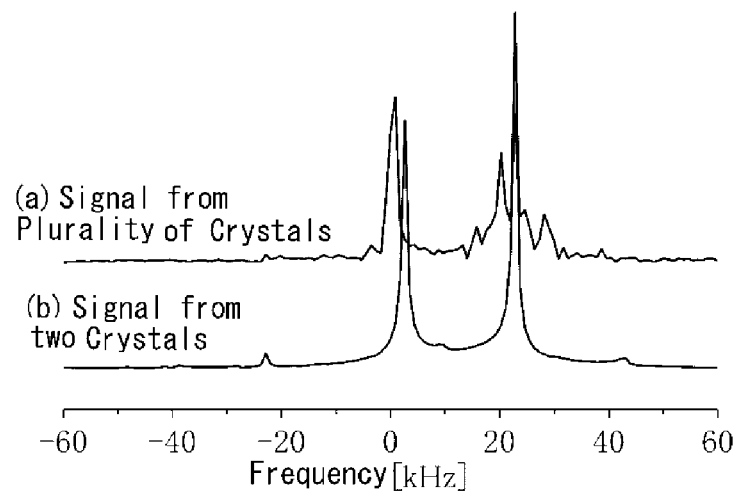
FIG. 26 is a diagram showing a piezoelectric effect signal received from a plurality of Rochelle salts having different resonance frequencies by an electric near-field probe having two resonance frequencies.

Further, it is recognized that when a plurality (two or more) of crystals having different resonance frequencies are brought close to the electric near-field probe, as shown in FIG. 26, piezoelectric crystals having slightly different resonance frequencies can simultaneously be detected.

(3) Receiving by Excitation Employing Frequency-Modulated Sine Burst Wave

Figure 27:
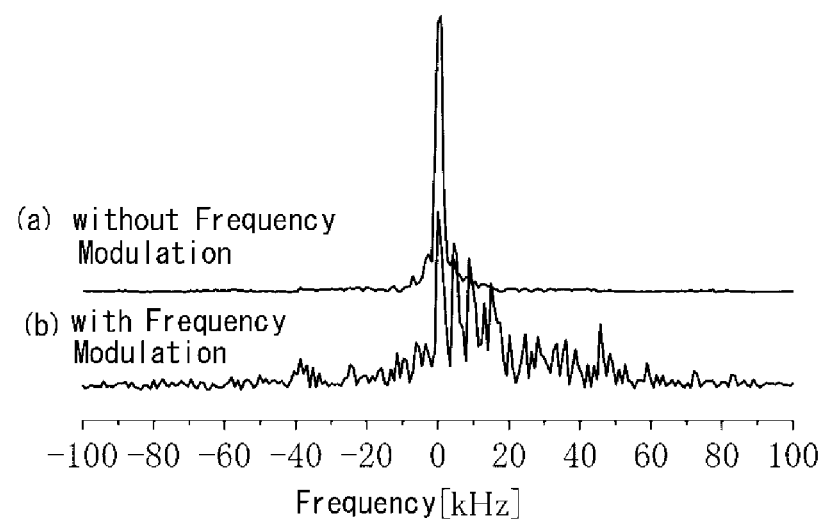
FIG. 27 is a diagram showing a piezoelectric effect signal received from a plurality of Rochelle salts excited by using a frequency-modulated sine burst wave.

When the frequency is modulated, the frequency band where piezoelectric crystals can be excited can be increased. FIG. 27 shows the measurement results with and without the modulation, in which piezoelectric effect signal was received from a plurality of Rochelle salt crystals (a grain diameter of 1 to 5 mm) by using the electric near-field probe shown in FIG. 1 and then the intensity was measured.

As seen from FIG. 27, in the situation with modulation, the frequency varies during excitation and hence the excitation time at a particular frequency is reduced on condition of a fixed bust time in comparison with a case of fixed frequency transmission. As a result, the signal intensity is reduced. On the other hand, the band where excitation can be achieved is increased by the modulation and hence more crystals can be detected.

(4) Receiving from Gradio Structure Type Electric Near-Field Probe

As described above, by virtue of the gradio structure, the electric field intensity at a distant place can be attenuated by approximately $1/10$ to $1/50$ in comparison with a case that the gradio structure is not employed. However, it has been found by an electromagnetic field simulator or the like that attenuation occurs also in the electric near-field.

Thus, comparison of the receiving intensity depending on the presence or absence of the gradio structure was performed by employing Rochelle salt crystals having a plurality of grain diameters serving as piezoelectric crystals. The results are as shown in FIG. 28.

Figure 28:
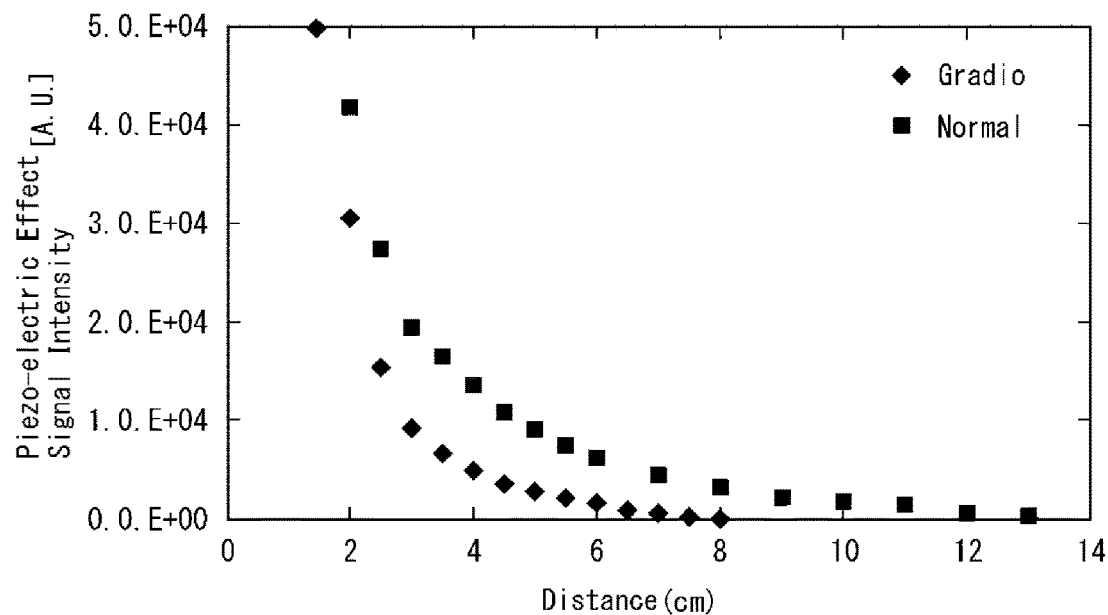
FIG. 28 is a diagram showing relations between the intensity of a piezoelectric effect signal and the distance from an electric near-field probe in electric near-field probes of gradio structure type and of normal type.

From FIG. 28, it is recognized that in a case that the output voltage of the transmission amplifier to be supplied to the electric near-field probe is set to be the same, regardless of the probe structure, almost the same detection sensitivity is achieved at a distance up to approximately 2 cm, but that when the distance becomes approximately 5 cm, in the case of gradio structure, the detection sensitivity is degraded to a fraction. However, considering the fact that the transmission field intensity at a distant place is reduced by approximately $1/10$ to $1/50$, the degradation in the receiving intensity at 5 cm or shorter can be recognized as within an allowable range. Further, when the gradio structure is employed, receiving of an extraneous noise can be reduced. Thus, as for the signal-noise ratio, the probe of gradio type structure achieved a more satisfactory result within 5 cm.

(5) Receiving from Piezoelectric Crystals Distributed Broadly

Figure 29:
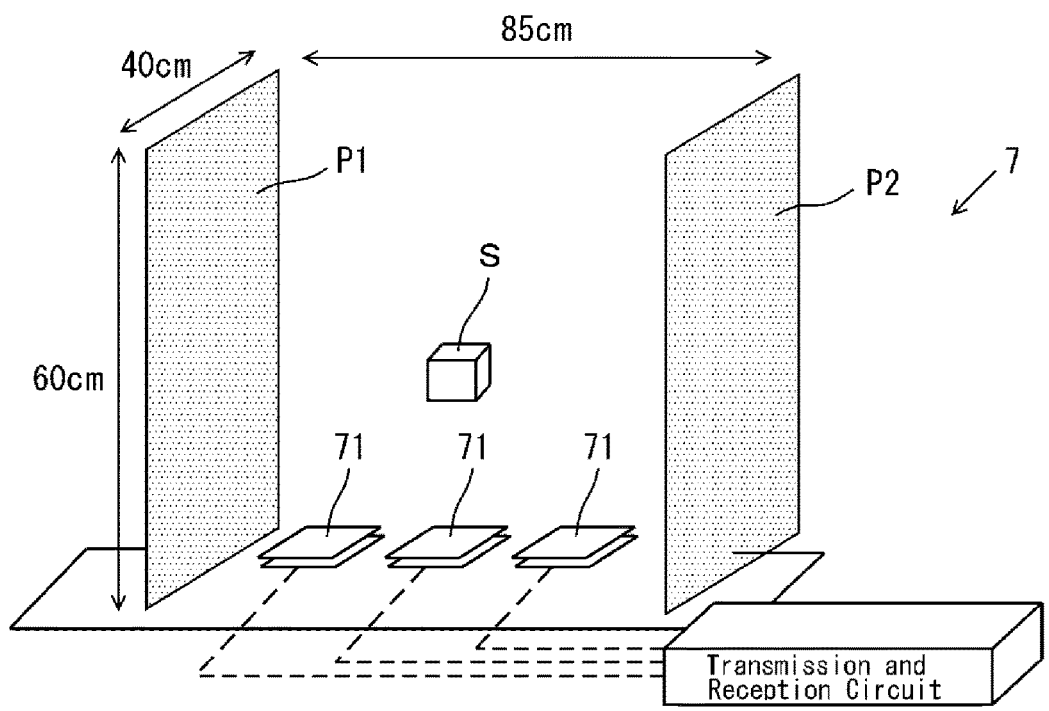
FIG. 29 is a perspective view schematically showing an example of a piezoelectric crystal detector in which plurality of electric near-field probes are arranged.

When piezoelectric crystals distributed broadly are to be detected, the piezoelectric crystals can efficiently be detected by employing the piezoelectric crystal detector shown in FIG. 29.

In FIG. 29, numeral 71 indicates an electric near-field probe. Numerals P1 and P2 indicate transmission plate electrodes. Then, a transmission circuit connected to the two transmission plate electrodes P1 and P2 and a reception circuit connected to a plurality of the electric near-field probes 71 are combined into one transmission and reception circuit. Here, in FIG. 29, three electric near-field probes 71 are arranged between the transmission plate electrodes P1 and P2 (60 cm long×40 cm wide) arranged vertically in parallel to each other at an interval of 85 cm. Then, symbol S indicates a sample serving as an inspection object which is inserted between the transmission plate electrodes P1 and P2.

When a transmission signal is inputted from the transmission circuit of the transmission and reception circuit into the transmission plate electrodes P1 and P2, an electric field is generated in a broad domain between the transmission plate electrodes P1 and P2 so that the entire inspection object S is excited. As a result, the entire inspection object S in the broad domain can sufficiently be excited so that a piezoelectric effect signal can be generated.

Figure 30:
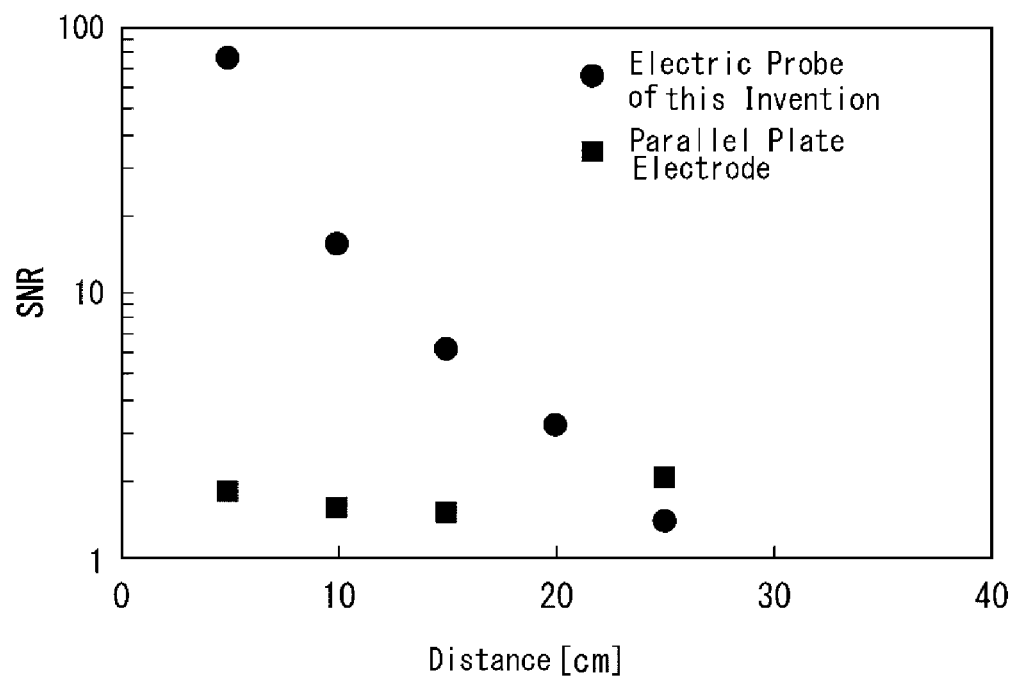
FIG. 30 is a diagram showing a piezoelectric effect signal received by using a piezoelectric crystal detector shown in FIG. 29.

FIG. 30 shows the piezoelectric effect signal received by the parallel plate electrodes or the electric near-field probe in a case that: the piezoelectric crystal detector of the present embodiment and a conventional piezoelectric crystal detector performing transmission and reception by using the two parallel plate electrodes were employed; 10 g of Rochelle salt was employed as an inspection object and placed in the center of the transmission plate electrodes with changing the height; and an electric field was applied with an electrode-to-electrode voltage of 1.8 kV.

In FIG. 30, the vertical axis indicates the SNR (the SN ratio; the signal-to-noise ratio) and the horizontal axis indicates the height at which the inspection object S was arranged. From FIG. 30, for example, it is recognized that when the distance from the electric near-field probe is as small as approximately 10 cm, the piezoelectric effect signal (●) received by the electric near-field probe is larger than the piezoelectric effect signal (■) received by the parallel plate type electrodes by a factor of approximately 10 and hence that when such a configuration is employed, in comparison with a case that transmission and reception are performed simply by using parallel plate electrodes, the receiving sensitivity is improved remarkably so that the inspection object distributed broadly can efficiently be detected.

8. Presence or Absence of Magnetic Ringing and Influence on Piezoelectric Effect Signal Receiving When an electric near-field probe is fabricated by employing an inductor constructed from an air-core coil without a toroidal core, in some cases, magnetic ringing is observed from metal or the like owing to a magnetic near-field generated from the coil.

Thus, magnetic ringing in a case that an inductor constructed from an air-core coil was employed and magnetic ringing in a case that an inductor constructed from a toroidal core was employed were compared. Specifically, since magnetic ringing also can be measured for a long time when resonance is caused at a particular frequency, a metal piece generating magnetic ringing at 1.37 MHz was prepared and then brought close to the electric near-field probe constructed from each inductor so that magnetic ringing was measured. The results are shown in FIG. 31.

Figure 31:
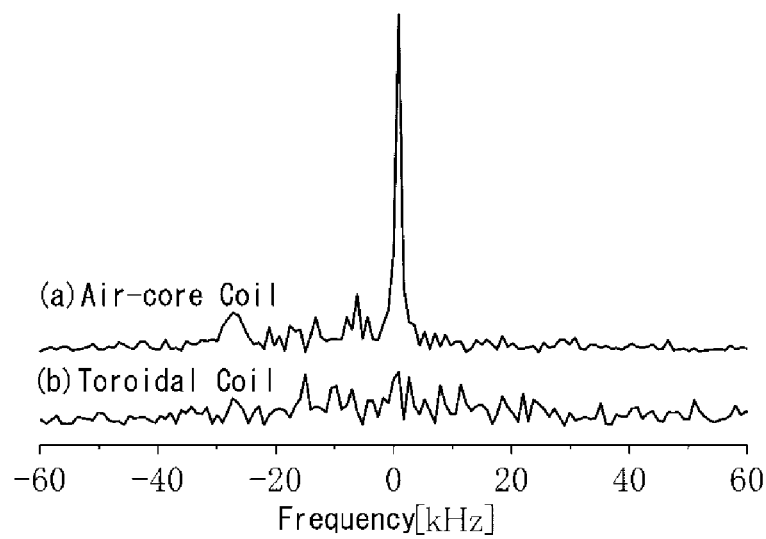
FIG. 31 is a diagram showing an example of measurement results of magnetic ringing in electric near-field probes whose inductors are different from each other.

From FIG. 31, it is recognized that in comparison with a case that an inductor constructed from an air-core coil was employed, magnetic ringing was suppressed in a case that an inductor constructed from a toroidal core was employed.

Next, the piezoelectric effect signal from a plurality of Rochelle salt crystals (to 5 mm) was received by employing the electric near-field probe constructed from each inductor. The results are shown in FIG. 32.

Figure 32:
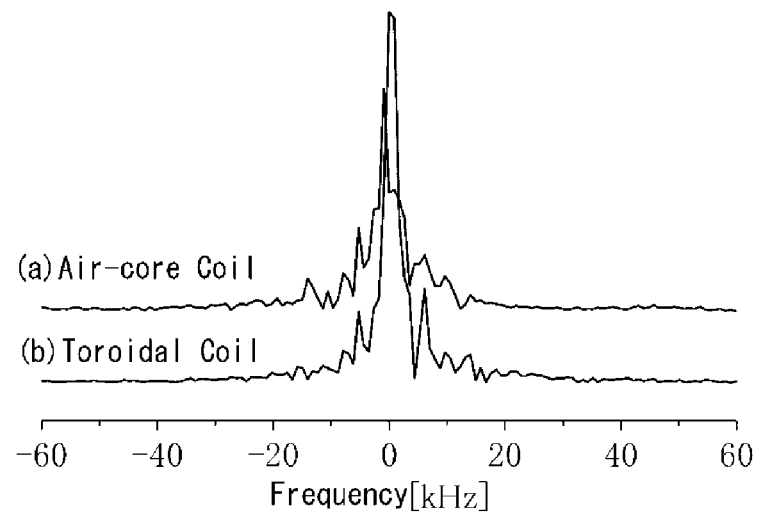
FIG. 32 is a diagram showing an example of measurement results of a piezoelectric effect signal in electric near-field probes whose inductors are different from each other.

From FIG. 32, it is recognized that the piezoelectric effect signal has been measured in each electric near-field probe. Thus, in a case that a sample composed of a piezoelectric substance and a metal piece or the like is to be inspected, when an inductor constructed from an air-core coil is employed, a possibility arises that a magnetic ringing signal is contained in the piezoelectric effect signal. Thus, high-accuracy inspection cannot be achieved. In contrast, when a case that an inductor constructed from a toroidal core is employed, magnetic ringing is suppressed and hence high-accuracy inspection can be achieved.

9. Influence of Electrically Conductive Material and Dielectric Material and Detection In an inspection employing an electric near-field probe, when a dielectric material or an electrically conductive material is present in the vicinity, in some cases, separately from a piezoelectric effect signal desired to be detected by the electric near-field probe, an external noise not originating from the piezoelectric effect becomes large. Thus, in some cases, the sensitivity is degraded and hence detection of a piezoelectric crystal becomes difficult. Thus, when an electrically conductive material such as a human body and a large metal can be detected by using the same electric near-field probe, degradation in the sensitivity of the inspection apparatus can be recognized in advance and hence an incorrect inspection that a piezoelectric crystal is not detected can be prevented.

Specifically, when a dielectric material or an electrically conductive material is present in the vicinity of the electric near-field probe of the present invention, in some cases, the resonance frequency slightly deviates or the Q factor is reduced owing to a loss in the inside of the conductor. This deviation in the frequency is caused mainly by fluctuation in the electrostatic capacitance of the capacitor of parallel plate type. According to an experiment by the present inventor, when the resonance frequency deviates, the intensity and the waveform of the transmission pulse vary.

Thus, when an electrically conductive material such as a human body and a large metal becomes detectable by using the electric near-field probe and utilizing such a property, an incorrect inspection that a piezoelectric crystal is not detected can be prevented.

Figure 33:
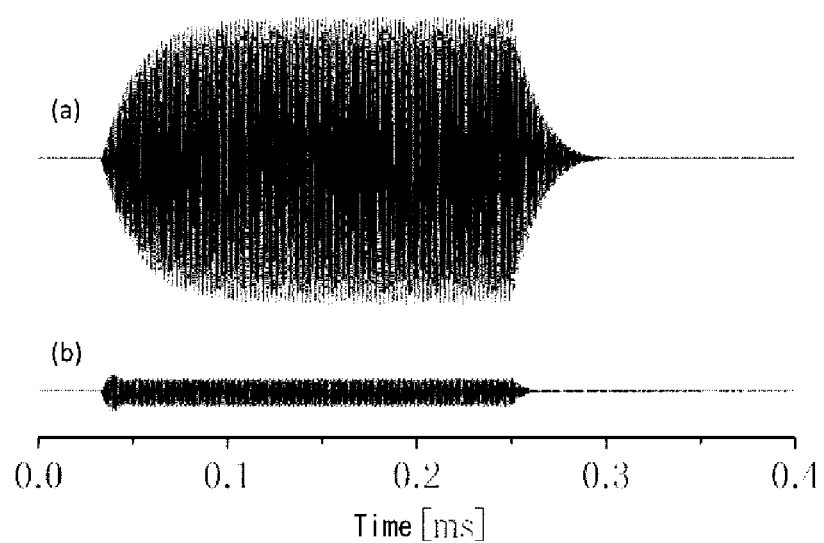
FIG. 33 is a diagram showing the shapes of a sine burst wave generated from an electric near-field probe in a case that a human body is present in the vicinity and in a case that a human body is not present.

FIG. 33 shows (a) the shape of a sine burst wave generated from the electric near-field probe of the present invention in a case that measurement was performed by using another electric near-field probe and (b) the shape of a sine burst wave generated from the electric near-field probe in a case that the hand is brought as close as a distance of 1 mm from the electric near-field probe of the present invention.

From FIG. 33, it is recognized that when the hand is brought close to the electric near-field probe, the intensity and the waveform of the transmission pulse vary. Further, it is recognized that when such a change is utilized, whether a metal, a human body, or the like is present in the vicinity can be judged. For example, when a residual voltage in the electric near-field probe is measured immediately after the termination of the excitation transmission wave, the intensity and the resonance characteristics of the excitation transmission wave can be estimated.

The present invention was illustrated based on the above embodiments. The present invention is not limited to the embodiments. The embodiments can be variously changed in the range which is the same as or equivalent to the present invention.

DESCRIPTION OF THE REFERENCE SIGNS 1, 2, 4, 71 Electric Near-Field Probe
11, 21a, 21b, 41a, 41b Capacitor
12, 22a, 22b, 42a, 42b inductor
13, 23a, 23b, 43 coaxial cable
24, 44, 111a, 111b metal plate
111c opening part
25, 45, 112 dielectric material
113 protection plate
7 piezoelectric crystal detector
72 control system
73 personal computer
C1, C2 Capacitor
D1, D2, D3, D4, D5, D6 diode
P1, P2 transmission plate electrode
S object to be inspected

What is claimed is:

1. An electric near-field probe comprising
   a series resonance circuit comprising a capacitor constructed such that a space between two metal plates arranged in parallel to each other is filled with a dielectric material or air and
   an inductor constructed such that a lead wire is wound around a toroidal core, wherein the capacitor and the inductor are connected in series so that the series resonance circuit has a predetermined resonance frequency,
   an electric near-field originating from a leakage electric field from the capacitor generated when an alternating voltage is applied to the series resonance circuit is transmitted to a piezoelectric crystal so that the piezoelectric crystal is excited and, at the same time, a piezoelectric effect signal generated from the excited piezoelectric crystal is received by the capacitor so that the piezoelectric effect signal is detected by the series resonance circuit.

2. The electric near-field probe according to claim 1, wherein an opening part is provided in a center portion of the metal plate opposing the piezoelectric crystal among the two metal plates constituting the capacitor.

3. The electric near-field probe according to claim 1, wherein the series resonance circuit is constructed from a plurality of series resonance circuits having different resonance frequencies.

4. The electric near-field probe according to claim 3, wherein in each of the plurality of series resonance circuits, resonance is achieved when an alternating voltage of a resonance frequency corresponding to each series resonance circuit is inputted.

5. The electric near-field probe according to claim 3, wherein in the plurality of series resonance circuits, resonance is achieved when a modulated alternating voltage is inputted.

6. The electric near-field probe according to claim 1, wherein two capacitors having the same shape and size are arranged and aligned in parallel to each other, then an inductor having the same shape and size is connected to each capacitor, and then the capacitors are connected to each other in reverse polarity so as to be constructed in a gradio structure type.

7. The electric near-field probe according to claim 1, wherein the series resonance circuit has a second capacitor connected in parallel to the capacitor, in which a terminal of the second capacitor is connected to the ground through a transmission/reception changeover switch, a control circuit for high-sensitivity receiving having a transmission amplifier and a receiving amplifier is provided, and
   the control circuit for high-sensitivity receiving is constructed such that, at the time of transmission, the transmission amplifier is connected in series to the electric near-field probe and at the same time the receiving amplifier is disconnected and at the time of receiving, the transmission amplifier is disconnected and, at the same time the receiving amplifier is connected in series to the electric near-field probe.

8. The electric near-field probe according to claim 1, wherein the series resonance circuit is provided with an amplifier circuit for transmission constructed such as to reduce a fall time of a transient phenomenon occurring in the electric near-field probe after termination of a transmission signal.

9. An electric near-field probe control system for controlling the electric near-field probe according to claim 1, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

10. A piezoelectric crystal detector comprising the electric near-field probe according to claim 1 and an electric near-field probe control system for controlling the electric near-field probe, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

11. A method of detecting an illicit drug which comprises contacting a sample with the piezoelectric crystal detector according to claim 10.

12. The piezoelectric crystal detector according to claim 10, employed in a non-contact key system.

13. A piezoelectric crystal detector, wherein a plurality of the electric near-field probes according to claim 1 are arranged between the plate electrodes arranged in parallel to each other.

14. The electric near-field probe according to claim 2, wherein the series resonance circuit is constructed from a plurality of series resonance circuits having different resonance frequencies.

15. An electric near-field probe control system for controlling the electric near-field probe according to claim 2, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

16. An electric near-field probe control system for controlling the electric near-field probe according to claim 3, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

17. An electric near-field probe control system for controlling the electric near-field probe according to claim 4, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

18. An electric near-field probe control system for controlling the electric near-field probe according to claim 5, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

19. An electric near-field probe control system for controlling the electric near-field probe according to claim 6, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

20. An electric near-field probe control system for controlling the electric near-field probe according to claim 7, wherein an alternating voltage is applied to the series resonance circuit having a predetermined resonance frequency so that an electric near-field originating from a leakage electric field generated in the capacitor is transmitted from the electric near-field probe so as to excite the piezoelectric crystal and, a piezoelectric effect signal generated from the excited piezoelectric crystal is received by the capacitor so that presence or absence or a property of the piezoelectric crystal is detected by the series resonance circuit.

* * * * *